(12) United States Patent
Doñate et al.

(10) Patent No.: US 7,098,187 B2
(45) Date of Patent: Aug. 29, 2006

(54) HUMAN KININOGEN D3 DOMAIN POLYPEPTIDE AS AN ANTI-ANGIOGENIC AND ANTI-TUMOR AGENT

(75) Inventors: Fernando Doñate, San Diego, CA (US); Andrew P. Mazar, San Diego, CA (US)

(73) Assignee: Attenuon, LLC, San Diego, CA (US)

( * ) Notice: Subject to any disclaimer, the term of this patent is extended or adjusted under 35 U.S.C. 154(b) by 0 days.

(21) Appl. No.: 10/661,784

(22) Filed: Sep. 15, 2003

(65) Prior Publication Data

US 2005/0058599 A1    Mar. 17, 2005

Related U.S. Application Data

(60) Provisional application No. 60/410,279, filed on Sep. 13, 2002.

(51) Int. Cl.
*A61K 38/00*    (2006.01)
*C07K 14/00*    (2006.01)

(52) U.S. Cl. .................... 514/12; 530/300; 530/350

(58) Field of Classification Search ................... 514/12
See application file for complete search history.

(56) References Cited

U.S. PATENT DOCUMENTS 6,284,726 B1    9/2001    Colman et al.
6,348,185 B1 *  2/2002    Piwnica-Worms .......... 424/1.69
6,869,931 B1 *  3/2005    McCrae ........................ 514/12
2004/0082517 A1  4/2004   Dewitt et al.

FOREIGN PATENT DOCUMENTS

WO    WO 00/27866    5/2000
WO    WO 00/35407    6/2000

OTHER PUBLICATIONS

Zhang et al. Can. J. Physiol. Pharmacol. 80: 85-90 (2002).*
WO 00/35407.*
Isordia-Salas, I. et al. Blood 102(8): 2835-2842 (2003).*

* cited by examiner

*Primary Examiner*—Jon Weber
*Assistant Examiner*—Anand Desai
(74) *Attorney, Agent, or Firm*—McKenna Long & Aldridge LLP

(57) ABSTRACT

Human kininogen domain 3 (HK-D3) polypeptides and biologically active variants and derivatives of HK-D3 are anti-angiogenic. These molecules are used to inhibit angiogenesis or treat a disease or condition in which angiogenesis is pathogenic. Because of their anti-angiogenic potential, these molecules are useful in the treatment of cancer by inhibiting or reversing the growth of primary or metastatic tumors.

17 Claims, 8 Drawing Sheets

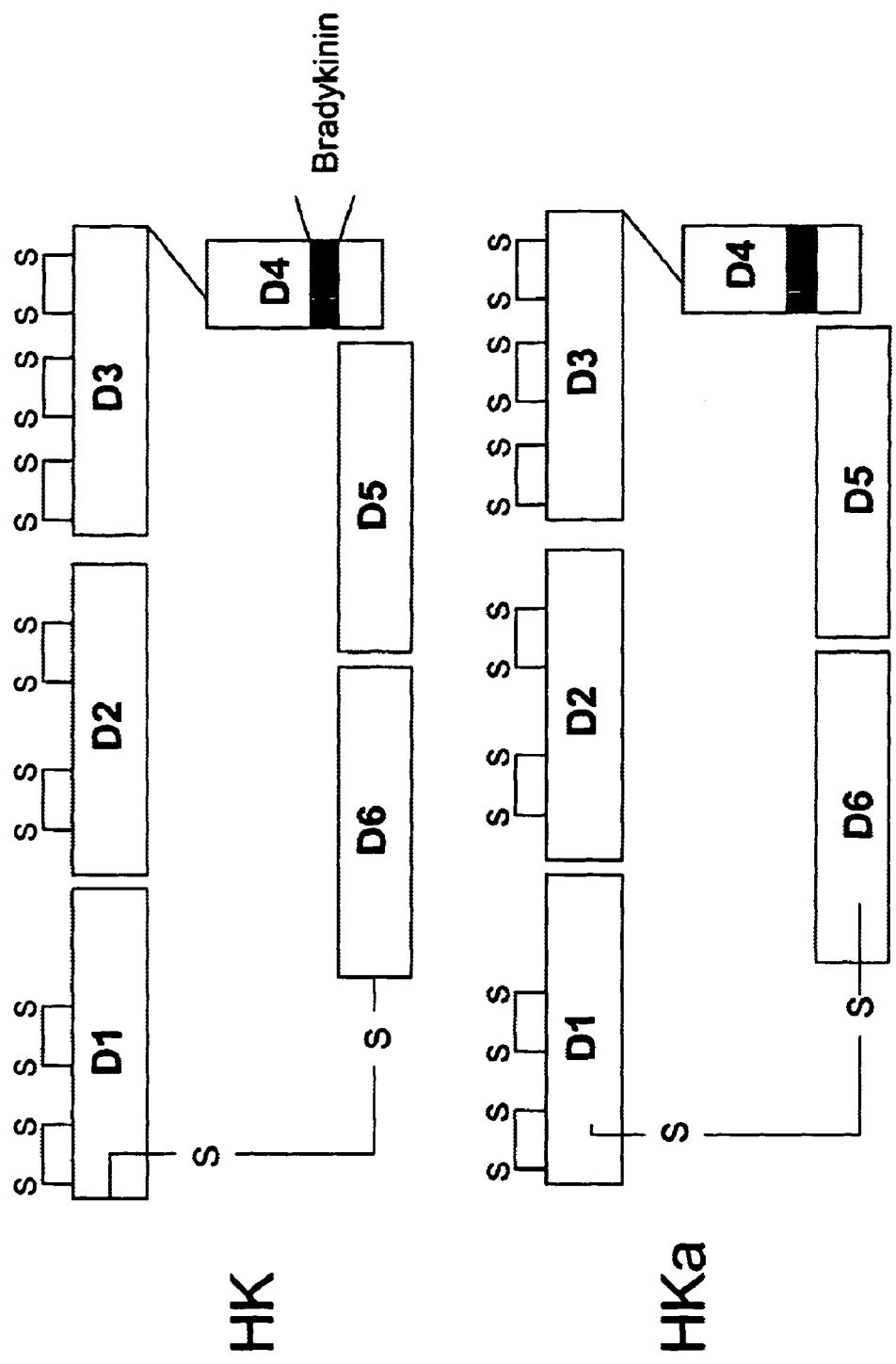
Fig. 1: Domain structure of Kininogen (HK)

HK-D3v expression and purification

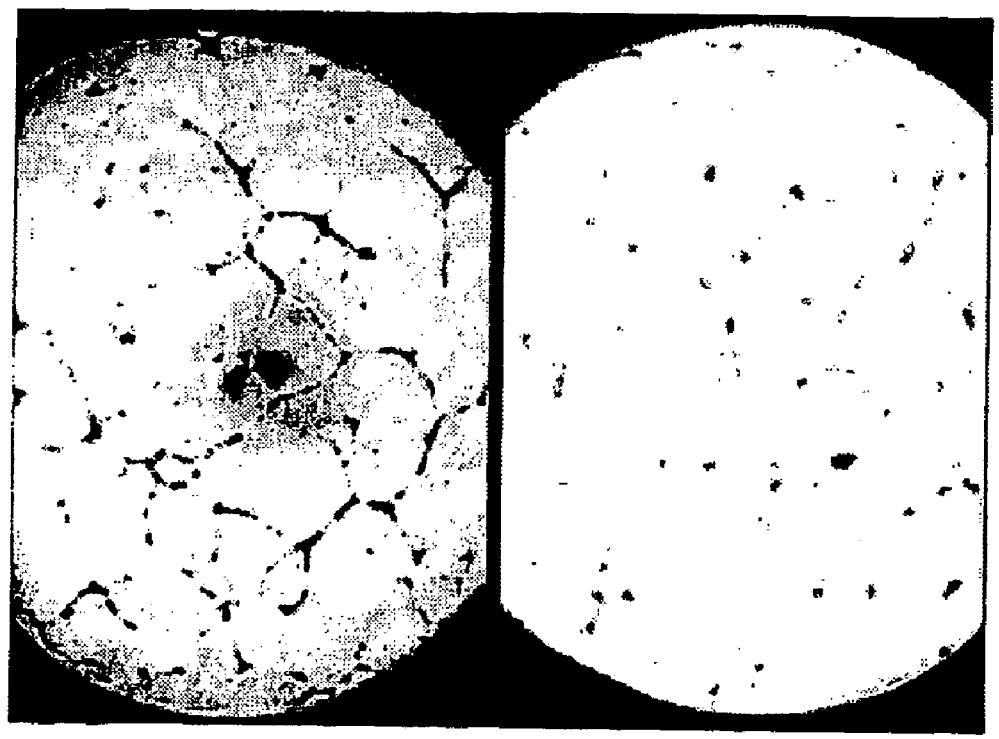
Fig. 4A  Control — HUVECs plated on Matrigel + bFGF
Fig. 4B  +D3v. — HUVECs plated on Matrigel + bFGF + 250 nM HK-D3v.

Fig. 5A Control — HUVECs plated on Matrigel + bFGF + VEGF + PMA
Fig. 5B +D3v — HUVECs plated on Matrigel + bFGF + VEGF + PMA + 250 nM HK-D3v.

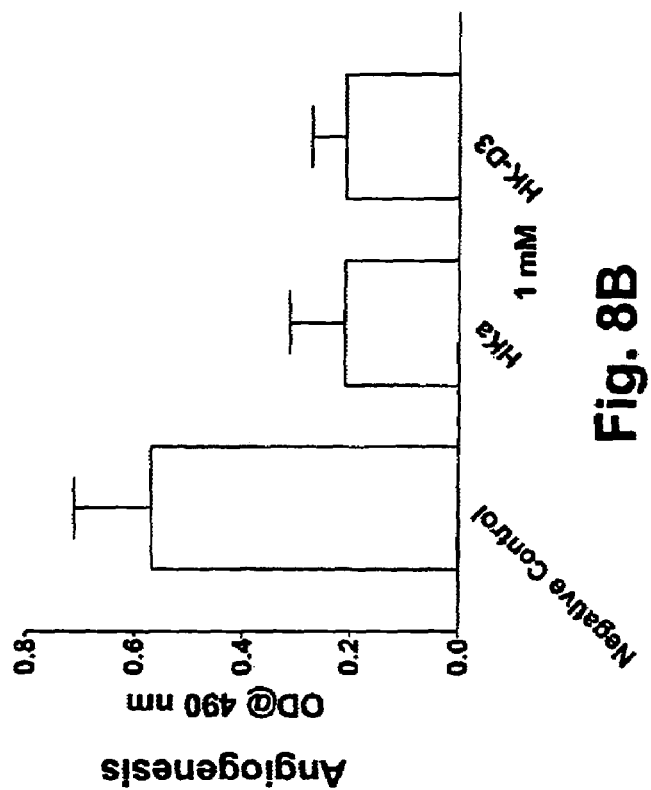
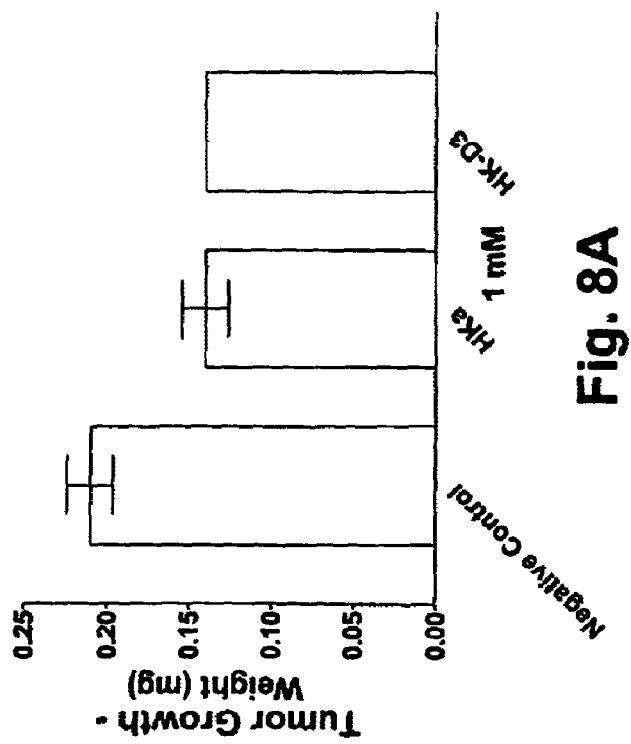

SEQUENCE LISTING

```
<160> NUMBER OF SEQ ID NOS: 6

<210> SEQ ID NO 1
<211> LENGTH: 123
<212> TYPE: PRT
<213> ORGANISM: Homo sapiens

<400> SEQUENCE: 1

Gly Lys Asp Phe Val Gln Pro Pro Thr Lys Ile Cys Val Gly Cys Pro
1               5                   10                  15

Arg Asp Ile Pro Thr Asn Ser Pro Glu Leu Glu Glu Thr Leu Thr His
            20                  25                  30

Thr Ile Thr Lys Leu Asn Ala Glu Asn Asn Ala Thr Phe Tyr Phe Lys
        35                  40                  45

Ile Asp Asn Val Lys Lys Ala Arg Val Gln Val Val Ala Gly Lys Lys
    50                  55                  60

Tyr Phe Ile Asp Phe Val Ala Arg Glu Thr Thr Cys Ser Lys Glu Ser
65                  70                  75                  80

Asn Glu Glu Leu Thr Glu Ser Cys Glu Thr Lys Lys Leu Gly Gln Ser
                85                  90                  95

Leu Asp Cys Asn Ala Glu Val Tyr Val Val Pro Trp Glu Lys Lys Ile
            100                 105                 110

Tyr Pro Thr Val Asn Cys Gln Pro Leu Gly Met
        115                 120

<210> SEQ ID NO 2
<211> LENGTH: 125
<212> TYPE: PRT
<213> ORGANISM: Homo sapiens

<400> SEQUENCE: 2

Gly Ser Gly Lys Asp Phe Val Gln Pro Pro Thr Lys Ile Cys Val Gly
1               5                   10                  15

Cys Pro Arg Asp Ile Pro Thr Asn Ser Pro Glu Leu Glu Glu Thr Leu
            20                  25                  30

Thr His Thr Ile Thr Lys Leu Asn Ala Glu Asn Asn Ala Thr Phe Tyr
        35                  40                  45

Phe Lys Ile Asp Asn Val Lys Lys Ala Arg Val Gln Val Val Ala Gly
    50                  55                  60
```

```
Lys Lys Tyr Phe Ile Asp Phe Val Ala Arg Glu Thr Thr Cys Ser Lys
 65                  70                  75                  80

Glu Ser Asn Glu Glu Leu Thr Glu Ser Cys Glu Thr Lys Lys Leu Gly
             85                  90                  95

Gln Ser Leu Asp Cys Asn Ala Glu Val Tyr Val Val Pro Trp Glu Lys
            100                 105                 110

Lys Ile Tyr Pro Thr Val Asn Cys Gln Pro Leu Gly Met
        115                 120                 125

<210> SEQ ID NO 3
<211> LENGTH: 127
<212> TYPE: PRT
<213> ORGANISM: Homo sapiens

<400> SEQUENCE: 3

Gly Ser Gly Lys Asp Phe Val Gln Pro Pro Thr Lys Ile Cys Val Gly
  1               5                  10                  15

Cys Pro Arg Asp Ile Pro Thr Asn Ser Pro Glu Leu Glu Glu Thr Leu
             20                  25                  30

Thr His Thr Ile Thr Lys Leu Asn Ala Glu Asn Asn Ala Thr Phe Tyr
         35                  40                  45

Phe Lys Ile Asp Asn Val Lys Lys Ala Arg Val Gln Val Val Ala Gly
     50                  55                  60

Lys Lys Tyr Phe Ile Asp Phe Val Ala Arg Glu Thr Thr Cys Ser Lys
 65                  70                  75                  80

Glu Ser Asn Glu Glu Leu Thr Glu Ser Cys Glu Thr Lys Lys Leu Gly
             85                  90                  95

Gln Ser Leu Asp Cys Asn Ala Glu Val Tyr Val Val Pro Trp Glu Lys
            100                 105                 110

Lys Ile Tyr Pro Thr Val Thr Val Asn His Trp Glu Cys Glu Phe
        115                 120                 125

<210> SEQ ID NO 4
<211> LENGTH: 369
<212> TYPE: DNA
<213> ORGANISM: Homo sapiens

<400> SEQUENCE: 4
gggaaggatt ttgtacaacc acctaccaag atttgcgtgg gctgccccag agatataccc      60
accaacagcc cagagctgga ggagacactg actcacacca tcacaaagct taatgcagag    120
aataacgcaa ctttctattt caagattgac aatgtgaaaa agcaagagt acaggtggtg      180 gctggcaaga atatttat tgacttcgtg gccagggaaa ccacatgttc caaggaaagt      240
aatgaagagt tgaccgaaag ctgtgagacc aaaaaacttg gccaaagcct agattgcaac    300
gctgaagttt atgtggtacc ctgggagaaa aaaatttacc ctactgtcaa ctgtcaacca    360
ctgggaatg                                                            369

<210> SEQ ID NO 5
<211> LENGTH: 375
<212> TYPE: DNA
<213> ORGANISM: Homo sapiens

<400> SEQUENCE: 5
ggatccggga aggattttgt acaaccacct accaagattt gcgtgggctg ccccagagat     60
atacccacca cagcccaga gctggaggag acactgactc acaccatcac aaagcttaat    120
gcagagaata acgcaacttt ctatttcaag attgacaatg tgaaaaaagc aagagtacag    180
```

-continued

```
gtggtggctg gcaagaaata ttttattgac ttcgtggcca gggaaaccac atgttccaag      240
gaaagtaatg aagagttgac cgaaagctgt gagaccaaaa aacttggcca aagcctagat      300
tgcaacgctg aagtttatgt ggtaccctgg gagaaaaaaa tttaccctac tgtcaactgt      360
caaccactgg gaatg                                                       375
```

<210> SEQ ID NO 6
<211> LENGTH: 381
<212> TYPE: DNA
<213> ORGANISM: Homo sapiens

<400> SEQUENCE: 6

```
ggatccggga aggattttgt acaaccacct accaagattt gcgtgggctg ccccagagat       60
atacccacca acagcccaga gctggaggag acactgactc acaccatcac aaagcttaat      120
gcagagaata acgcaacttt ctatttcaag attgacaatg tgaaaaaagc aagagtacag      180
gtggtggctg gcaagaaata ttttattgac ttcgtggcca gggaaaccac atgttccaag      240
gaaagtaatg aagagttgac cgaaagctgt gagaccaaaa aacttggcca aagcctagat      300
tgcaacgctg aagtttatgt ggtaccctgg gagaaaaaaa tttaccctac tgtcactgtc      360
aaccactggg aatgtgaatt c                                                381
```

HUMAN KININOGEN D3 DOMAIN POLYPEPTIDE AS AN ANTI-ANGIOGENIC AND ANTI-TUMOR AGENT

CROSS-REFERENCE TO RELATED APPLICATIONS

This application claims priority to U.S. Provisional patent application Ser. No. 60/410,279, filed on Sep. 13, 2002.

BACKGROUND OF THE INVENTION

1. Field of the Invention

The present invention in the field of biochemistry and medicine is directed to angiogenesis-inhibitory polypeptides comprising a part of human kininogen, particularly, the D3 domain (HK-D3) and variants thereof, and their use in diagnosis and therapy of diseases associated with endothelial cell migration and proliferation. In particular these polypeptides are useful in treating subjects with cancer.

2. Description of the Background Art

Angiogenesis, the formation of new capillaries form pre-existing ones (Folkman, J., *N. Engl. J. Med.,* 1971, 285:1182–1186; Hanahan D. et al., *Cell,* 1996, 86:353–364), is a normal part of embryonic development, wound healing and female reproductive function. However, angiogenesis also plays a pathogenic role in the establishment and progression of certain diseases. Cancer, rheumatoid arthritis and diabetic retinopathy are examples of such diseases (Carmeliet P. et al., *Nature,* 2000,407:249–257). Anti-angiogenic therapy holds promise in inhibiting the progression of these diseases.

Angiogenesis can be triggered by several pro-angiogenic cytokines. In the setting of cancer, tumor cells under hypoxic conditions secrete vascular endothelial growth factor (VEGF) and/or fibroblast growth factor (bFGF). These proteins diffuse and bind to specific receptors on endothelial cells (ECs) in the local vasculature, perturbing the balance of pro- and anti-angiogenic forces in favor of angiogenesis. As a consequence of binding these proteins, ECs are activated to (a) secrete enzymes that induce remodeling of the associated tissue matrix, and (b) change the patterns and levels of expression of adhesion molecules such as integrins. Following matrix degradation, ECs proliferate and migrate toward the hypoxic tumor, resulting in the generation and maturation of new blood vessels.

Interestingly, many anti-angiogenic factors result from the degradation of matrix proteins—i.e., are a result of the action of pro-angiogenic enzymes. Examples include endostatin, a fragment of collagen XIII (O'Reilly, M. S. et al., *Cell* 1997, 88:277–285); kringle 5 of plasminogen (O'Reilly, M. S. et al., *Cell,* 994, 79:315–328) and PEX, the C-terminus non-catalytic subunit of MMP-2 (Brooks P C et al., *Cell,* 1998, 92:391–400).

The concept has emerged that, due to the abundance of pro-angiogenic factors, these anti-angiogenic molecules are unable to overcome the pro-angiogenic balance in a primary tumor. However, since they are secreted into circulation, these anti-angiogenic molecules are capable of inhibiting angiogenesis at other locations where tumor cells may have begun to invade. Consequently, micro-metastases comprising these tumor cells at these new locations remain dormant. This hypothesis explains the puzzling observation made by surgeons many years ago: at various times after surgical removal of a primary tumor in a patient with no obvious metastatic disease, the patient returns with advanced metastatic disease.

Thus, clinical intervention by treatment with one or more of the anti-angiogenic factors could inhibit the angiogenic process and halt tumor growth as well as metastasis. Significant evidence in the literature (cited above) supports this notion.

Biochemistry of High Molecular Weight Kininogen

Two forms of kininogen, high molecular weight kininogen (HK, $M_r$=120 kDa), and low molecular weight kininogen (LK, $M_r$=68 kDa), have been identified in human plasma (Jacobsen S et al., *Br J Pharm* 29:25–36, 1967). HK is an α-globulin with a plasma concentration of 90 µg/ml (Proud D et al., *J Lab Clin Med* 95:563–5574, 1980) (FIG. 1), and LK is a α-globulin with a plasma concentration of 220 µg/ml (Muller-Esterl W et al., *Biochim Biophys Acta* 106:145–152, 1982). These proteins are derived from the alternative splicing of a single gene (Kitamura N et al., *J Biol Chem* 260:8610–8617, 1985), and share a common heavy (H) chain, which contains domains 1, 2 and 3, termed D1, D2 and D3 (Colman R W et al., *Blood* 90:3819–3843, 1997). However, while LK contains only a 4 kDa light (L) chain ($D4_L$), the ~46 kDa L chain of HK contains domains 5 and 6 (D5 and D6, respectively).

Each domain of HK has a unique function. For example, D1 binds calcium, and D2 inhibits calpain (Colman et al., supra). The cell binding regions of HK are contained within D3 and D5, while D6 binds plasma prekallikrein and coagulation Factor XI. In intact HK, D4 links the H and L chains; D4 also includes the nonapeptide, bradykinin (BK) which is released from HK by kallikrein via cleavage between $Lys_{362}$-$Arg_{363}$ and $Arg_{371}$-$Ser_{372}$, leaving behind a cleaved molecule consisting of a 62 kDa H chain and 56–62 kDa L chain, which are bonded by an intrachain disulfide between $Cys_{10}$ and $Cys_{596}$. A subsequent cleavage at a site near the N-terminus of D5, results in reduction of the $M_r$ of the L chain to ~45 kDa (Kaplan A P et al., *Blood* 70:1–15, 1987).

Released BK is a potent vasodilator and an agonist for ECs. Kallikrein-mediated cleavage of HK occurs on the EC surface, and may be mediated (a) directly by plasma kallikrein or (b) after binding of prekallikrein to cell-bound K, followed by its activation to kallikrein by an EC cysteine protease. Thus the EC is an important site for $HK_a$ generation. Phorbol myristoyl acetate (PMA)-stimulated ECs bind increased amounts of HK (Colman et al., supra) suggesting acceleration of this process on "activated" ECs. The observation that ECs produce HK mRNA and protein further supports the physiological importance of this process (Schmaier A H et al., *J Biol Chem* 263:16327–16333, 1988).

The release of BK from HK is accompanied by a structural rearrangement in the remaining two-chain kininogen molecule, $HK_a$ and the acquisition of several novel properties. For example, cleavage of HK to $HK_a$ allows the latter to bind to artificial anionic surfaces (Colman et al., supra); interactions that are mediated by residues of the His-Gly-rich region within D5 of $HK_a$ (amino acids 420–458) (DeLacadena R A et al., *Protein Sci* 1:151–160, 1992; Kunapuli S P et al., *J Biol Chem* 268:2486–2492, 1993).

Furthermore, $HK_a$, but not HK, is anti-adhesive, inhibiting the spreading of osteosarcoma and melanoma cells on vitronectin, and of ECs, platelets and mononuclear cells on vitronectin and fibrinogen (Asakura S et al., *J Cell Biol* 116:465–476, 1992). The structural rearrangement of $HK_a$ involves a change in the orientation of $HK_a$ domains relative to each other.

HK exists as a linear array of three linked globular regions, with the two peripheral regions connected by a thin strand (Colman R W et al., *J Clin Invest* 100:1481–1487, 1997). The strand may represent the disulfide bridge between D1 and D6, as it is no longer apparent following reduction. Studies with epitope-specific monoclonal antibodies (mAbs) determined that the globular domains on the ends of HK represent the prekallikrein-binding region (within D6 of the L chain) and the cysteine protease inhibitor region (D2 and D3 of the H chain), while the central nodule represents the anionic surface binding region within D5.

After kallikrein-mediated cleavage, the two-chain molecule, $HK_a$, retains the trinodular structure, though the three globular regions rearrange in a pattern resembling vertices of a triangle. In this structure, the anionic surface binding and prekallikrein binding regions are more closely apposed. Because the EC binding regions within HK have been mapped to sites within D3 of the H chain and D5 of the L chain ((Reddigari S R et al., *Blood* 81:1306–1311, 1993; Herwald H et al., *J Biol Chem* 270:14634–14642, 1995; Hasan A et al., *J Biol Chem* 269:31822–31830, 1994; Hasan A et al., *J Mol Biol* 219:717–725, 1995) and since the latter regions in the linear sequence overlap extensively with the anionic surface binding regions of $HK_a$, the orientation of the cellular binding regions within HK and $HK_a$ must differ. This conclusion implies that HK and $HK_a$ are likely to interact differently with ECs, a hypothesis supported by functional studies demonstrating that $HK_a$, but not HK, is a potent inhibitor of proliferation and inducer of apoptosis in ECs.

Interactions of HK with ECs

A. Identification of Cell Binding Regions within HK

HK was reported to bind with high affinity to human umbilical vein ECs (HUVEC) (Reddigari et al., supra; van Iwaarden F et al., *J Biol Chem* 263:4698–4703, 1988; Zini J M et al., *Blood* 81:2936–2946, 1993; Hasan A et al., *Blood* 85:3134–3143, 1995). The presence of $Zn^{2+}$ is an absolute requirement for binding, whereas $Ca^{2+}$ either inhibited or had no effect on binding. Internalization of HK has also been reported (van Iwaarden F et al., *Blood* 71:1268–1276, 1988).

The binding of HK to ECs is mediated through interactions involving both its H and L chains, and several studies have led to the identification of specific regions that mediate binding within D3 (Herwald H et al., supra) and D5 (Hasan et al., *J. Mol. Biol.*, supra) (one of which overlaps with the BK sequence within D4). These regions were identified by the ability of synthetic peptides with corresponding sequences to compete with intact, labeled HK for binding to HUVEC.

In contrast to HK, little information is available concerning the binding of $HK_a$ to ECs. In one study, cleavage of biotinylated HK by increasing amounts of kallikrein led to a progressive diminution in binding of the cleaved ligand. In contrast, others reported that $HK_a$ was more potent than unlabeled HK in inhibiting the binding of radiolabeled HK to ECs ($IC_{50}$=73 nM for $HK_a$ vs 335 nM for HK) (Reddigari et al., supra). Although these $IC_{50}$ values are difficult to reconcile with a reported $K_d$ (30–40 nM) for the binding of HK to ECs, they nevertheless suggest differences between HK and $HK_a$ in their interactions with cells.

B. Endothelial Cell HK/$HK_a$ Receptors $HK_a$ inhibition of EC proliferation in vitro is a unique property of $HK_a$ as HK, which binds to ECs, nevertheless lacks this antiproliferative effect. Moreover, the observed difference in binding to ECs exhibited by HK and $HK_a$ suggests potential differences in function. $HK_a$ could inhibit EC proliferation by several mechanisms. First, it might induce detachment of ECs from their matrix through direct interactions with integrins, thereby leading to interruption of integrin-mediated signaling and MAP kinase phosphorylation, leading to apoptosis. However, other than one report that single-chain HK binds to Mac-1 ($\alpha_M\beta_2$ or CD11b/CD18) on monocytes, there is no evidence for interactions of kininogen with integrins.

The binding of $HK_a$ to ECs was also not inhibited by a blocking antibody against the $\beta_3$ integrin chain, suggesting that $HK_a$ does not interact with $\alpha_v\beta_3$, an integrin which plays an important role in angiogenesis (Colman R W et al., *J Clin Invest* 100:1481–1487, 1997). $HK_a$ might interact in either a specific or non-specific manner with an ECM protein(s), thereby preventing its interaction with an EC integrin receptor. However, there is no data to support this hypothesis. The fact that $HK_a$ inhibited the proliferation of HUVEC plated on fibronectin, gelatin, and Matrigel, suggested effects independent of matrix identity. $HK_a$ might inhibit the binding of growth factors to cellular glycosaminoglycans, such as heparan sulfate, or to specific growth factor receptors. However, this explanation is unlikely, since withdrawal of growth factors does not lead to EC apoptosis within 6 hours—a time frame in which $HK_a$ induced apoptotic changes.

McCrae's group recently observed that the cleaved form of $HK_a$ inhibited bFGF-stimulated angiogenesis in vivo. (Zhang J-C et al., *FASEB J.* 14:2589–600, 2000). In vitro, $HK_a$ potently inhibited the proliferation of HUVEC and human dermal microvascular ECs (HDMVEC), inducing EC apoptosis. Several peptides were identified with sequences corresponding to the binding regions within D3 and D5 of $HK_a$ that inhibited EC proliferation at low µM to nM concentrations. Comparison of the sequences of overlapping peptides used in these studies led to the identification peptides of 4–8 amino acids that mediated this activity. Compared to the antiproliferative effects, the anti-adhesive effects of $HK_a$ appear to be of less importance since EC adhesion was only modestly inhibited at $HK_a$ concentrations >100 nM, whereas anti-proliferative effects were observed at concentrations as low as ~1 nM. McCrae (WO 00/35407; PCT/US99/28465) has described variants of the 8-mer peptide $X_1$-Asn-Asn-Ala-Thr-Phe-Tyr-Phe-Lys-$X_2$, which are discussed in the context of EXAMPLE I.

SUMMARY OF THE INVENTION

The present inventors have discovered that HK-D3 polypeptides and other biologically active derivatives of HK-D3, exhibit anti-angiogenic and anti-tumor activity. The anti-angiogenic action may occur in part through inhibition of oxidative stress, which has recently been demonstrated in vitro to contribute to the pathophysiology of angiogenesis (Brown et al. (2000) *Cancer Res.* 60:6298). Oxidative stress leading to angiogenesis may require transition metals such as zinc and copper—small molecule copper chelators have been demonstrated to inhibit tumor growth in vivo (Brewer, G J, International Patent publication WO/013712 (2000)).

The present invention includes the first demonstration that HK-D3 and a variant thereof inhibit angiogenesis. The present invention provides novel methods to inhibit or reduce angiogenesis, tumor growth, EC proliferation, EC migration or EC tube formation using HK-D3 or its biologically active variants or derivatives.

Transition metals and oxidative stress have been implicated in the etiology of non-cancerous diseases, especially, neurodegenerative diseases such as Alzheimer's disease, Parkinson's disease and amyotrophic lateral sclerosis (ALS). The present invention also provides compositions and methods for the treatment of any of these and other diseases whose pathobiology involves abnormal presence or undesired action of transition metals, including conditions where the presence of the transition metal may induce oxidative stress.

The present invention is directed to an isolated anti-angiogenic polypeptide having the sequence of HK-D3v (SEQ ID NO:2 or a variant thereof, or a variant of native HK-D3 (SEQ ID NO:1), which has substantially the same or greater biological activity, and preferably at least about 20% of the biological activity, of native HK-D3 in inhibiting angiogenesis, endothelial cell proliferation or endothelial tube formation in an in vitro or in vivo bioassay.

Also provided is a diagnostically or therapeutically labeled anti-angiogenic polypeptide as labeled above with a diagnostic or therapeutic label. A diagnostically useful HK-D3-related composition comprises (a) the above diagnostically labeled polypeptide; and (b) a diagnostically acceptable carrier.

A preferred detectable label includes a radionuclide, a PET-imageable agent, an MRI-imageable agent, a fluorescer, a fluorogen, a chromophore, a chromogen, a phosphorescer, a chemilurninescer or a bioluminescer. Preferred radionuclides are $^3H$, $^{14}C$, $^{35}S$, $^{67}Ga$, $^{68}Ga$, $^{72}As$, $^{89}Zr$, $^{97}Ru$, $^{99}Tc$, $^{111}In$, $^{123}I$, $^{125}I$, $^{131}I$, $^{169}Yb$ and $^{201}Tl$.

Preferred fluorescers are fluorescein, rhodamine, dansyl, phycoerythrin, phycocyanin, allophycocyanin, o-phthaldehyde, fluorescamine, a fluorescein derivative, Oregon Green, Rhodamine Green, Rhodol Green and Texas Red.

The invention is also directed to an anti-angiogenic pharmaceutical composition comprising an effective amount of the polypeptide described above and a pharmaceutically acceptable carrier. A preferred therapeutic anti-angiogenic pharmaceutical composition comprises (a) an effective amount of a therapeutically labeled polypeptide as described above to which is bound directly or indirectly a therapeutically active moiety; and (b) a pharmaceutically acceptable carrier. Preferably, the therapeutic composition is in a form suitable for injection.

One class of preferred therapeutically active moieties are radionuclides, preferably selected from the group consisting of $^{47}Sc$, $^{67}Cu$, $^{90}Y$, $^{109}Pd$, $^{125}I$, $^{131}I$, $^{186}Re$, $^{188}Re$, $^{199}Au$, $^{211}At$, $^{212}Pb$ and $^{217}Bi$.

Also provided is a method for inhibiting cell migration, cell invasion, cell proliferation or angiogenesis, or for inducing apoptosis, comprising contacting cells associated with undesired cell migration, invasion, proliferation or angiogenesis with an effective amount of the polypeptide described above, preferably a pharmaceutical composition as above.

In another embodiment, the invention provides an isolated nucleic acid that encodes the polypeptide of claim 1. Preferred nucleic acids are those having SEQ ID NO:3 or SEQ ID NO:4, or homologues or variants thereof that encode biologically active anti-angiogenic peptides.

Also provided is an expression vector comprising the above nucleic acid operatively linked to (a) a promoter, and (b) optionally, additional regulatory sequences that regulate expression of the nucleic acid in a eukaryotic cell. The expression vector may be a plasmid or a viral vector.

In another embodiment, this invention is directed to a cell, preferably a mammalian cells, most preferably a human cell, transformed or transfected with the above nucleic acid molecule or expression vector This invention includes a method for providing to a cell, tissue or organ an angiogenesis-inhibitory amount of HK-D3, HK-D3v, or a variant thereof, comprising administering to the cell tissue or organ, the above expression vector, such that the nucleic acid is taken up and expressed in the cell, tissue or organ. This administering is preferably in vivo.

In another embodiment of the method, an angiogenesis-inhibitory amount of HK-D3, HK-D3v, or a variant thereof is provided to a cell, tissue or organ by contacting, preferably in vivo, the cell tissue or organ, with the transformed or transfected cells described above, wherein the administered cells express the polypeptide.

Also provided is a method for inhibiting angiogenesis in a subject in need of such inhibition, comprising administering to the subject an effective amount of the above expression vector such that the nucleic acid is expressed resulting in the presence of an angiogenesis-inhibiting amount of the polypeptide, thereby inhibiting the angiogenesis.

In another embodiment, the method for inhibiting angiogenesis in a subject in need of such inhibition comprises administering to the subject an effective amount of the transformed or transfected cells as above, which cells produce and provide in the subject an angiogenesis-inhibiting amount of the polypeptide, thereby inhibiting the angiogenesis.

The above methods may be used to treat a subject, preferably a human, who has a tumor, wherein the angiogenesis inhibition results in reduction in size or growth rate of the tumor or destruction of the tumor.

In yet another embodiment, the invention is directed to an affinity ligand useful for binding to or isolating an HK-D3-binding molecule or cells expressing the binding molecule, comprising a polypeptide as described above immobilized to a solid support or carrier.

A method for isolating a HK-D3-binding molecule from a complex mixture comprises:
(a) contacting the mixture with the above affinity ligand;
(b) allowing material in the mixture to bind to the-ligand;
(c) removing unbound material from the ligand; and
(d) eluting the bound HK-D3-binding molecule, thereby isolating the HK-D3 binding molecule.

A method for isolating or enriching cells expressing a HK-D3-binding site or receptor from a cell mixture, comprises
(a) contacting the cell mixture with the above affinity ligand;
(b) allowing any cells expressing the binding site or receptor to bind to the affinity ligand;
(c) separating cells bound to the affinity ligand from unbound cells; and
(d) removing the bound cells from the affinity ligand, thereby isolating or enriching the HK-D3 binding site-expressing cells.

BRIEF DESCRIPTION OF THE DRAWINGS

FIG. 1 is a schematic diagram of the structure of HK showing the domain architecture of high molecular kininogen (HK) and activated high molecular weight kininogen (HKa).

FIGS. 4A and 4B show the inhibition of FGF-stimulated EC tube formation on Matrigel® as a test of angiogenesis. Matrigel® was plated into 96 well plates. bFGF (10 ng/mL) stimulated tube formation by HUVEC (12,000 cells/well). HK D3v (250 nM) inhibited tube formation. The plates were evaluated by two independent readers after 24 hours of incubation at 37° C.

FIGS 5A and 5B show the inhibition of EC tube formation on Matrigel® stimulated by the combination of bFGF (10 ng/mL), VEGF (1 ng/mL) and PMA (20 nM) as for FIGS. 4A and 4B). Here too, 250 nM HK-D3v inhibited tube formation.

FIG. 8A compares the tumor growth inhibitory activity of HKa and HK-D3 (1 μM) expressed as tumor weight, in the MLL model above. FIG. 8B compares the angiogenesis-inhibitory activity of HKa and HK-D3 (1 μM) as reflected in tumor Hb concentrations (determined by the Drabkin's method).

DESCRIPTION OF THE PREFERRED EMBODIMENTS

Figures 2A, 2B:
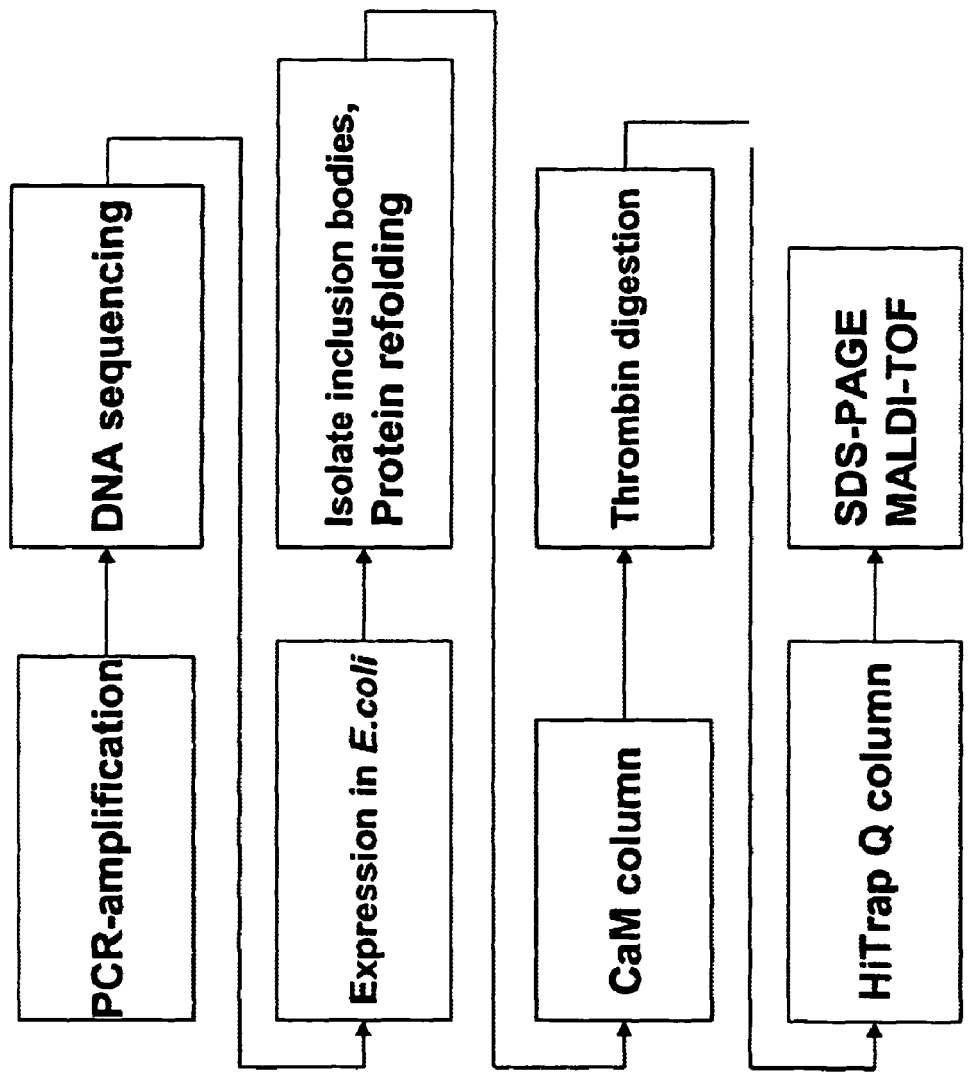
FIG. 2A shows the expression and purification scheme for HK-D3, which was expressed in *E. coli* as a fusion protein, CBP-HK-D3, comprising calmodulin binding protein (CBP) and HK-D3. The cDNA for domain 3 of kininogen was PCR-amplified from a full-length HK cDNA and inserted into pCAL-n (Stratagene). *E. coli* were transformed with this expression vector and induced with 1 mM IPTG. Cells were harvested and the supernatants and inclusion bodies analyzed by SDS-PAGE. CBP-HK-D3 was found predominantly in the inclusion bodies and was purified from isolated inclusion bodies after refolding by dilution in TBS, pH 8.0 containing a glutathione redox buffer. The refolded protein was first passed through a Calmodulin (CaM) affinity resin (Stratagene). The CBP portion was removed by controlled thrombin digestion and the HK-D3 further purified with a HiTrap Q™ resin (Pharmacia) The fractions were analyzed by SDS-PAGE, those containing HK-D3 pooled, dialyzed and the molecular mass of the sample determined by MALDI-TOF.
FIG. 2B shows a gel of the final HK-D3v pool.

No role for the complete HK-D3 polypeptide as an inhibitor of angiogenesis had been suggested prior to the making of the present invention. The present inventors conceived that native HK-D3 and biologically active HK-D3 polypeptides, homologues, variants and other functional derivatives exhibit anti-angiogenic activity and, therefore, anti-tumor activity. Pharmaceutical compositions comprising these compounds are useful in the treatment of cancer and other diseases associated with aberrant or undesired angiogenesis.

Native HK-D3 has a length of 123 amino acids and a molecular weight of 14007 Da. The amino acid sequence, SEQ ID NO:1, is:

```
  1    GKDFVQPPTK ICVGCPRDIP TNSPELEETL THTITKLNAE NNATFYFKID NVKKARVQVV
 61    AGKKYFIDFV ARETTCSKES NEELTESCET KKLGQSLDCN AEVYVVPWEK KIYPTVNCQP
121    LGM
```

An N-terminal addition variant of HK-D3, designated HK-D3v(GS), that includes an additional Gly Ser sequence at the N-terminus (underscored below) results as a byproduct of the expression system. Its sequence is shown below (SEQ ID NO:2).

```
  1    GSGKDFVQPP TKICVGCPRD IPTNSPELEE TLTHTITKLN AENNATFYFK IDNVKKARVQ
 61    VVAGKKYFID FVARETTCSK ESNEELTESC ETKKLGQSLD CNAEVYVVPW EKKIYPTVNC
121    QPLGM
```

Another variant of HK-D3, designated HK-D3v (shown below as SEQ ID NO:3), which the present inventors cloned and expressed and tested in the Examples below, has a length of 127 amino acids and a molecular weight of 14409 Da. First, the N-terminal G and S are not part of the native HK-D3 sequence. The additions at the N-terminus and replacements/additions at the C-terminus are underscored.

```
  1    GSGKDFVQPP TKICVGCPRD IPTNSPELEE TLTHTITKLN AENNATFYFK IDNVKKARVQ    SEQ ID NO:3
 61    VVAGKKYFID FVARETTCSK ESNEELTESC ETKKLGQSLD CNAEVYVVPW EKKIYPTVTV
121    NHWECEF
```

As used herein, the term "HK-D3" will be understood to refer to domain-3 peptides of HK including biologically active homologues such as substitution or addition variants of native HK-D3 and other variants of such homologues that share the anti-angiogenic and anti-tumor properties of HK-D3v as exemplified herein.

Native HK-D3 is encoded by DNA having the following sequence (SEQ ID NO:4):

```
GGGAAGGATTTTGTACAACCACCTACCAAGATTTGCGTGGGCTGCCCCAG
AGATATACCCACCAACAGCCCAGAGCTGGAGGAGACACTGACTCACACCA
TCACAAAGCTTAATGCAGAGAATAACGCAACTTTCTATTTCAAGATTGAC
AATGTGAAAAAAGCAAGAGTACAGGTGGTGGCTGGCAAGAAATATTTTAT
TGACTTCGTGGCCAGGGAAACCACATGTTCCAAGGAAAGTAATGAAGAGT
TGACCGAAAGCTGTGAGACCAAAAAACTTGGCCAAAGCCTAGATTGCAAC
GCTGAAGTTTATGTGGTACCCTGGGAGAAAAAAATTTACCCTACTGTCAA
CTGTCAACCACTGGGAATG
```

DNA encoding HK-D3v(GS) has the following nucleotide sequence (SEQ ID NO:5):

```
GGATCCGGGAAGGATTTTGTACAACCACCTACCAAGATTTGCGTGGGCTG
CCCCAGAGATATACCCACCAACAGCCCAGAGCTGGAGGAGACACTGACTC
ACACCATCACAAAGCTTAATGCAGAGAATAACGCAACTTTCTATTTCAAG
ATTGACAATGTGAAAAAAGCAAGAGTACAGGTGGTGGCTGGCAAGAAATA
TTTTATTGACTTCGTGGCCAGGGAAACCACATGTTCCAAGGAAAGTAATG
AAGAGTTGACCGAAAGCTGTGAGACCAAAAAACTTGGCCAAAGCCTAGAT
TGCAACGCTGAAGTTTATGTGGTACCCTGGGAGAAAAAAATTTACCCTAC
TGTCAACTGTCAACCACTGGGAATG
```

DNA encoding HK-D3v has the following nucleotide sequence (SEQ ID NO:6):

```
GGATCCGGGAAGGATTTTGTACAACCACCTACCAAGATTTGCGTGGGCTG
CCCCAGAGATATACCCACCAACAGCCCAGAGCTGGAGGAGACACTGACTC
ACACCATCACAAAGCTTAATGCAGAGAATAACGCAACTTTCTATTTCAAG
ATTGACAATGTGAAAAAAGCAAGAGTACAGGTGGTGGCTGGCAAGAAATA
TTTTATTGACTTCGTGGCCAGGGAAACCACATGTTCCAAGGAAAGTAATG
AAGAGTTGACCGAAAGCTGTGAGACCAAAAAACTTGGCCAAAGCCTAGAT
TGCAACGCTGAAGTTTATGTGGTACCCTGGGAGAAAAAAATTTACCCTAC
TGTCACTGTCAACCACTGGGAATGTGAATTC
```

Other homologues or variants of the native HK-D3 polypeptide that share sequence similarity also exhibit anti-angiogenic and anti-tumor activity.

A functional homologue must possess the biochemical and biological activity of the native molecule, preferably the anti-angiogenic and anti-tumor activity, which can be tested using in vitro or in vivo methods described herein or others well-known in the art. In view of this functional characterization, use of homologous kininogen D3 proteins from other species, including proteins not yet discovered, falls within the scope of the invention if these proteins have sequence similarity and the recited biochemical and biological activity.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred method of alignment, Cys residues are aligned.

In a preferred embodiment, the length of a sequence being compared is at least 30%, preferably at least 40%, more preferably at least 50%, even more preferably at least 60%, and even more preferably at least 70%, 80%, or 90% of the length of the reference sequence. For example, preferred alignment would be with HK-D3 (SEQ ID NO:1) or HK-D3v (SEQ ID NO:2), at least 30%, preferably at least 40%, more preferably at least 50%, even more preferably at least 60% and even more preferably at least 70, 80 or 90% of the amino acid residues are aligned. The amino acid residues (or nucleotides from the coding sequence) at corresponding amino acid (or nucleotide) positions are then compared. When a position in the first sequence is occupied by the same amino acid residue (or nucleotide) as the corresponding position in the second sequence, then the molecules are identical at that position (as used herein amino acid or nucleic acid "idenfity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J. Mol. Biol. 48:444–453 (1970) algorithm which has been incorporated into the GAP program in the GCG software package (available at The World Wide Web URL: gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at the website having the URL "gcg.com", using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers et al. (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403–10. BLAST nucleotide searches can be performed with the NBLAST program, score=100, wordlength=12 to obtain nucleotide sequences homologous to human or murine HK-D3 nucleic acid molecules. BLAST protein searches can be performed with the XBLAST program, score=50, wordlength=3 to obtain amino acid sequences homologous to the native HK-D3 protein and its homologues. To obtain gapped alignments for comparison purposes, Gapped BLAST can be utilized as described in Altschul et al. (1997) *Nucl Acids Res.* 25:3389–3402. When utilizing BLAST and Gapped BLAST programs, the default parameters of the respective programs (e.g., XBLAST and NBLAST) can be used. See the website having the URL "ncbi.nlm.nih.gov."

Thus, a homologue of the HK-D3 described above is characterized as having (a) functional activity of native HK-D3 or of HK-D3v, and (b) sequence similarity to a native HK-D3 or HK-D3v when determined as above, of at least about 30% (at the amino acid level), preferably at least about 50%, more preferably at least about 70%, even more preferably at least about 90%.

It is within the skill in the art to obtain and express such a protein using DNA probes based on the disclosed sequences of HK-D3 and HK-D3v. Then, the protein's biochemical and biological activity can be tested readily using art-recognized methods such as those described herein. A biological assay of endothelial cell proliferation will indicate whether the homologue has the requisite activity to qualify as a "functional" homologue.

Polypeptide Compositions

A preferred composition is, or comprises, a biologically active variant or derivative of HK-D3 characterized in that it possesses the binding activity and/or biological activity of HK-D3. Such binding is to a ligand (or "receptor") that is preferably a member of the following "classes:"
(1) thrombospondin, or
(2) an endothelial cell surface molecule.

HK-D3 may bind similarly to other molecules that interact with these two types of "ligands." Thus, the present invention preferably includes any HK-D3 homologue, variant or derivative hat binds specifically to thrombospondin or endothelial cells.

Moreover, a biologically active polypeptide as intended here has HK-D3 activity in an in vitro or in vivo assay of binding or an assay of biological activity, such as those described herein. Preferably the polypeptide inhibits endothelial cell proliferation or migration, EC tube formation, angiogenesis or tumor growth with activity at least about 20% of the activity of HK-D3 or of HK-D3v.

The polypeptide may be capped at its N and C termini with an acyl (abbreviated "Ac")—and an amido (abbreviated "Am") group, respectively, for example acetyl ($CH_3CO$—) at the N terminus and amido (—$NH_2$) at the C terminus.

A broad range of N-terminal capping functions, preferably in a linkage to the terminal amino group, is contemplated, for example:
formyl;
alkanoyl, having from 1 to 10 carbon atoms, such as acetyl, propionyl, butyryl;
alkenoyl, having from 1 to 10 carbon atoms, such as hex-3-enoyl;
alkynoyl, having from 1 to 10 carbon atoms, such as hex-5-ynoyl;
aroyl, such as benzoyl or 1-naphthoyl;
heteroaroyl, such as 3-pyrroyl or 4-quinoloyl;
alkylsulfonyl, such as methanesulfonyl;
arylsulfonyl, such as benzenesulfonyl or sulfanilyl;
heteroarylsulfonyl, such as pyridine-4-sulfonyl;
substituted alkanoyl, having from 1 to 10 carbon atoms, such as 4-aminobutyryl;
substituted alkenoyl, having from 1 to 10 carbon atoms, such as 6hydroxy-hex-3-enoyl;
substituted alkynoyl, having from 1 to 10 carbon atoms, such as 3-hydroxy-hex-5-ynoyl;
substituted aroyl, such as 4chlorobenzoyl or 8-hydroxynaphth-2-oyl;
substituted heteroaroyl, such as 2,4-dioxo-1,2,3,4-tetrahydro-3-methyl-quinazolin-6-oyl;
substituted alkylsulfonyl, such as 2-aminoethanesulfonyl;
substituted arylsulfonyl, such as 5-dimethylamino-1-naphthalenesulfonyl;
substituted heteroarylsulfonyl, such as 1-methoxy-6-isoquinolinesulfonyl;
carbamoyl or thiocarbamoyl;
substituted carbamoyl (R'—NH—CO) or substituted thiocarbamoyl (R'—NH—CS) wherein R' is alkyl, alkenyl, alkynyl, aryl, heteroaryl, substituted alkyl, substituted alkenyl, substituted alkynyl, substituted aryl, or substituted heteroaryl;
substituted carbamoyl (R'—NH—CO) and substituted thiocarbamoyl (R'—NH—CS) wherein R' is alkanoyl, alkenoyl, alkynoyl, aroyl, heteroaroyl, substituted alkanoyl, substituted alkenoyl, substituted alkynoyl, substituted aroyl, or substituted heteroaroyl, all as above defined.

The C-terminal capping function can either be in an amide or ester bond with the terminal carboxyl. Capping functions that provide for an amide bond are designated as $NR^1R^2$ wherein $R^1$ and $R^2$ may be independently drawn from the following group:
hydrogen;
alkyl, preferably having from 1 to 10 carbon atoms, such as methyl ethyl, isopropyl;
alkenyl, preferably having from 1 to 10 carbon atoms, such as prop-2-enyl;
alkynyl, preferably having from 1 to 10 carbon atoms, such as prop-2-ynyl;
substituted alkyl having from 1 to 10 carbon atoms, such as hydroxyalkyl, alkoxyalkyl, mercaptoalkyl, alkylthioalkyl, halogenoalkyl, cyanoalkyl, aminoalkyl, alkylaminoalkyl, dialkylaminoalkyl, alkanoylalkyl, carboxyalkyl, carbamoylalkyl;
substituted alkenyl having from 1 to 10 carbon atoms, such as hydroxyalkenyl, alkoxyalkenyl, mercaptoalkenyl, alkylthioalkenyl, halogenoalkenyl, cyanoalkenyl,aminoalkenyl, alkylaminoalkenyl, dialkylaminoalkenyl, alkanoylalkenyl, carboxyalkenyl, carbamoylalkenyl;
substituted alkynyl having from 1 to 10 carbon atoms, such as hydroxyalkynyl, alkoxyalkynyl, mercaptoalkynyl, alkylthioalkynyl, halogenoalkynyl, cyanoalkynyl, aminoalkynyl, alkylaminoalkynly, dialkylaminoalkynyl, alkanoylalkynyl, carboxyalkynyl, carbamoylalkynyl;
aroylalkyl having up to 10 carbon atoms, such as phenacyl or 2-benzoylethyl;
aryl, such as phenyl or 1-naphthyl;
heteroaryl, such as 4-quinolyl;
alkanoyl having from 1 to 10 carbon atoms, such as acetyl or butyryl;
aroyl, such as benzoyl;
heteroaroyl, such as 3-quinoloyl;
OR' or NR'R" where R' and R" are independently hydrogen, alkyl, aryl, heteroaryl, acyl, aroyl, sulfonyl, sulfinyl, or $SO_2$—R''' or SO—R''' where R''' is substituted or unsubstituted alkyl, aryl, heteroaryl, alkenyl, or alkynyl.

Capping functions that provide for an ester bond are designated as OR, wherein R may be: alkoxy; aryloxy;

heteroaryloxy; aralkyloxy; heteroaralkyloxy; substituted alkoxy; substituted aryloxy; substituted heteroaryloxy; substituted aralkyloxy; or substituted heteroaralkyloxy.

Either the N-terminal or the C-terminal capping function, or both, may be of such structure that the capped molecule functions as a prodrug (a pharmacologically inactive derivative of the parent drug molecule) that undergoes spontaneous or enzymatic transformation within the body in order to release the active drug and that has improved delivery properties over the parent drug molecule (Bundgaard H, Ed: *Design of Prodrugs*, Elsevier, Amsterdam, 1985).

Judicious choice of capping groups allows the addition of other activities on the peptide. For example, the presence of a sulfhydryl group linked to the N- or C-terminal cap will permit conjugation of the derivatized peptide to other molecules.

Production of Polypeptides and Derivatives

General Chemical Synthetic Procedures

The polypeptides of the invention are preferably be prepared using recombinant DNA technology although they may also be prepared using solid-phase synthesis, such as that generally described by Merrifield, J. Amer. Chem. Soc., 85:2149–54 (1963), although other equivalent chemical syntheses known in the art are also useful. Solid-phase peptide synthesis may be initiated from the C-terminus of the peptide by coupling a protected α-amino acid to a suitable resin. Such a starting material can be prepared by attaching an α-amino-protected amino acid by an ester linkage to a chloromethylated resin or to a hydroxymethyl resin, or by an amide bond to a BHA resin or MBHA resin. Such methods, well-known in the art, are disclosed, for example, in U.S. Pat. 5,994,309 which is incorporated by reference in its entirety.

Amino Acid Substitution and Addition Variants

Also included in this invention are polypeptides in which at least one amino acid residue and preferably, between one and five, more preferably between one and three, have been replaced compared to the native sequence. For a detailed description of protein chemistry and structure, see Schulz, G E et al., *Principles of Protein Structure*, Springer-Verlag, New York, 1979, and Creighton, T E, *Proteins: Structure and Molecular Principles*, W. H. Freeman & Co., San Francisco, 1984, which are hereby incorporated by reference. The preferred types of substitutions are conservative substitutions which are defined herein as exchanges within one of the following groups:

1. Small aliphatic, nonpolar or slightly polar residues: e.g., Ala, Ser, Thr, Gly;
2. Polar, negatively charged residues and their amides: e.g. Asp, Asn, Glu, Gln;
3. Polar, positively charged residues: e.g., His, Arg, Lys;

Pro, because of its unusual geometry, tightly constrains the chain. More substantial changes in functional properties are made by selecting substitutions that are less conservative, such as between, rather than within, the above groups (or two other amino acid groups not shown above), which will differ more significantly in their effect on maintaining (a) the structure of the peptide backbone in the area of the substitution (b) the charge or hydrophobicity of the molecule at the target site, or (c) the bulk of the side chain Most substitutions according to the present invention are those that do not produce radical changes in the functional characteristics of the peptide molecule. Even when it is difficult to predict the exact effect of a substitution in advance of doing so, one skilled in the art will appreciate that the effect can be evaluated by routine screening assays, preferably the biological assays or binding assays described below. Modifications of peptide properties including redox or thermal stability, hydrophobicity, susceptibility to proteolytic degradation or the tendency to aggregate with carriers or into multimers are tested by methods well known to those of skill.

The present invention provides methods to inhibit or reduce angiogenesis, tumor growth, EC proliferation, EC migration or EC tube formation.

The invention also provides pharmaceutical compositions comprising polypeptide or peptide homologues, variants or other derivatives of HK-D3.

The nucleotide sequence (SEQ ID NO:4) and amino acid sequence (SEQ ID NO:1) of HK-D3 are derived from the sequence of the full length HK protein and DNA or shorter fragments that are available from GenBank (e.g., GenBank Accession number AH005302 and Swiss Prot number: P01042).

Although HK-D3 may be derived from cleavage of intact HK that is isolated from a body fluid such as blood or urine, a tissue extracts or as a product of a cell line growing in culture that produces "native" HK-D3 or that has been genetically modified with DNA encoding native HK-D3 or encoding a functional variant thereof to express the polypeptide or variant.

HK-D3 polypeptides or derivatives are most preferably produced by recombinant methods including from prokaryotic sources such as *E. coli* as described in more detail below. Recombinant techniques known in the art include, but are not limited to DNA amplification using PCR of a cDNA library for example by reverse transcription of mRNA in cells extracts followed by PCR.

Basic texts disclosing general methods of molecular biology, all of which are incorporated by reference, include: Sambrook, J. et al., *Molecular Cloning: A Laboratory Manual*, 2$^{nd}$ Edition, Cold Spring Harbor Press, Cold Spring Harbor, N.Y., 1989; Ausubel, F M et al. *Current Protocols in Molecular Biology*, Vol. 2, Wiley-Interscience, New York, (current edition); Kriegler, *Gene Transfer and Expression: A Laboratory Manual* (1990); Glover, D M, ed, *DNA Cloning: A Practical Approach*, vol. I & II, IRL Press, 1985; Albers, B. et al., *Molecular Biology of the Cell*, 2$^{nd}$ Ed., Garland Publishing, Inc., New York, N.Y. (1989); Watson, J D et al., *Recombinant DNA*, 2$^{nd}$ Ed., Scientific American Books, New York, 1992; and Old, R W et al., *Principles of Gene Manipulation: An Introduction to Genetic Engineering*, 2$^{nd}$ Ed., University of California Press, Berkeley, Calif. (1981).

Chemical Derivatives of HK-D3

"Chemical derivatives" of HK-D3 contain additional chemical moieties not normally a part of the protein. Covalent modifications of the polypeptide are included within the scope of this invention. Such derivatized moieties may improve the solubility, absorption, biological half life, and the like. Moieties capable of mediating such effects are disclosed, for example, in *Remington's Pharmaceutical Sciences*, 16$^{th}$ ed., Mack Publishing Co., Easton, Pa. (1980).

Such modifications may be introduced into the molecule by reacting targeted amino acid residues of the polypeptide with an organic derivatizing agent that is capable of reacting with selected side chains or terminal residues. Another modification is cyclization of the protein.

Cysteinyl residues most commonly are reacted with α-haloacetates (and corresponding amines) to give carboxymethyl or carboxyamidomethyl derivatives. Cysteinyl residues also are derivatized by reaction with bromotrifluoroacetone, α-bromo-β-(5-imidozoyl) propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate (pH 5.5–7.0) which agent is relatively specific for the histidyl side chain. p-bromophenacyl bromide also is useful; the reaction is preferably performed in 0.1 M sodium cacodylate at pH 6.0.

Lysinyl and amino terminal residues are derivatized with succinic or other carboxylic acid anhydrides. Derivatization with a cyclic carboxylic anhydride has the effect of reversing the charge of the lysinyl residues. Other suitable reagents for derivatizing amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, including phenylglyoxal, 2,3-butanedione, 1,2-cyclohexanedione, and ninhydrin Such derivatization requires that the reaction be performed in alkaline conditions because of the high $pK_a$ of the guanidine functional group. Furthermore, these reagents may react with the groups of lysine as well as the arginine ε-amino group.

Modification of tyrosyl residues has permits introduction of spectral labels into a polypeptide. This is accomplished by reaction with aromatic diazonium compounds or tetranitromethane. Most commonly, N-acetylimidizol and tetranitromethane are used to create O-acetyl tyrosyl species and 3-nitro derivatives, respectively.

Carboxyl side groups, aspartyl or glutamyl, may be selectively modified by reaction with carbodiimides (R—N=C=N—R') such as 1-cyclohexyl-3-(2-morpholinyl-(4-ethyl) carbodiimide or 1-ethyl-3-(4-azonia4,4-dimethylpentyl) carbodiimide. Furthermore, aspartyl and glutamyl residues can be converted to asparaginyl and glutaminyl residues by reaction with ammonia.

Aspartyl and glutamyl residues are converted to asparaginyl and glutaminyl residues by reaction with ammonium ions. Conversely, glutaminyl and asparaginyl residues may be deamidated to the corresponding glutamyl and aspartyl residues. Deamidation can be performed under mildly acidic conditions. Either form of these residues falls within the scope of this invention.

Derivatization with bifunctional agents is useful for cross-linking the polypeptide to a water-insoluble support matrix or other macromolecular carrier. Commonly used cross-linking agents include 1,1-bis(diazoacetyl)-2-phenylethane, glutaraldehyde, N-hydroxysuccinimide esters, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane.

Derivatizing agents such as methyl-3-[(p-azidophenyl) dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of the hydroxyl groups of seryl or threonyl residues, methylation of the α-amino groups of lysine, arginine, and histidine side chains (Creighton, supra), acetylation of the N-terminal amine, and, in some instances, aridation of the C-terminal carboxyl groups.

Also included are polypeptides wherein one or more D-amino acids are substituted for one or more L-amino acids.

Diagnostic and Prognostic Compositions

The polypeptide or peptide of the invention can be detectably labeled and used, for example, to detect a polypeptide binding protein ligand or a cellular binding site/receptor, such as the binding sites on ECs described above, whether on the surface or in the interior of a cell. The fate of the polypeptide during and after binding can be followed in vitro or in vivo by using the appropriate method to detect the label. The labeled polypeptide may be utilized in vivo for diagnosis and prognosis, for example to image occult metastatic foci or for other types of in situ evaluations.

The term "diagnostically labeled" means that the polypeptide has attached to it a diagnostically detectable label. There are many different labels and methods of labeling known to those of ordinary skill in the art, described below. General classes of labels which can be used in the present invention include radioactive isotopes, paramagnetic isotopes, and compounds which can be imaged by positron emission tomography (PET), fluorescent or colored compounds, etc. Suitable detectable labels include radioactive, fluorescent, fluorogenic, chromogenic, or other chemical labels. Useful radiolabels (radionuclides), which are detected simply by gamma counter, scintillation counter or autoradiography include $^3H$, $^{125}I$, $^{131}I$, $^{35}S$ and $^{14}C$. $^{131}I$ is also a useful therapeutic isotope (see below).

A number of U.S. patents, incorporated by reference herein, disclose methods and compositions for complexing metals to larger molecules, including description of useful chelating agents. The metals are preferably detectable metal atoms, including radionuclides, and are complexed to proteins and other molecules. These documents include: U.S. Pat. No. 5,627,286 (Heteroatom-bearing ligands and metal complexes thereof); U.S. Pat. No. 5,618,513 (Method for preparing radiolabeled peptides); U.S. Pat. No. 5,567,408; U.S. Pat. No. 5,443,816 (Peptide-metal ion pharmaceutical preparation and method); U.S. Pat. No. 5,561,220 (Tc—$^{99m}$ labeled peptides for imaging inflammation).

Common fluorescent labels include fluorescein, rhodamine, dansyl, phycoerythrin, phycocyanin, allophycocyanin, o-phthaldehyde and fluorescamine. The fluorophore, such as the dansyl group, must be excited by light of a particular wavelength to fluoresce. See, for example, Haugland, *Handbook of Fluorescent Probes and Research Chemicals*, Sixth Ed., Molecular Probes, Eugene, Oreg., 1996). Fluorescein, fluorescein derivatives and fluorescein-like molecules such as Oregon Green™ and its derivatives, Rhodamine Green™ and Rhodol Green™, are coupled to amine groups using the isothiocyanate, succinimidyl ester or dichlorotriazinyl-reactive groups. Similarly, fluorophores may also be coupled to thiols using maleimide, iodoacetamide, and aziridine-reactive groups. The long wavelength rhodamines, which are basically Rhodamine Green™ derivatives with substituents on the nitrogens, are among the most photostable fluorescent labeling reagents known. Their spectra are not affected by changes in pH between 4 and 10, an important advantage over the fluoresceins for many biological applications. This group includes the tetramethylrhodamines, X-rhodamines and Texas Red™ derivatives. Other preferred fluorophores for derivatizing the polypeptide according to this invention are those which are excited by ultraviolet light. Examples include cascade blue, coumarin derivatives, naphthalenes (of which dansyl chloride is a member), pyrenes and pyridyloxazole derivatives. Also included as labels are two related inorganic materials that have recently been described: semiconductor nanocrystals, comprising, for example, cadmium sulfate (Bruchez, M. et al., *Science* 281:2013–2016 (1998), and quantum dots, e.g., zinc-sulfide-capped Cd selenide (Chan, W C et al., *Science* 281:2016–2018 (1998)).

In yet another approach, the amino group of the polypeptide is allowed to react with reagents that yield fluorescent products, for example, fluorescamine, dialdehydes such as o-phthaldialdehyde, naphthalene-2,3-dicarboxylate and anthracene-2,3-dicarboxylate. 7-nitrobenz-2-oxa-1,3diazole (NBD) derivatives, both chloride and fluoride, are useful to modify amines to yield fluorescent products.

The polypeptides of the invention can also be labeled for detection using fluorescence-emitting metals such as $^{152}$Eu, or others of the lanthanide series. These metals can be attached to the polypeptide using such metal chelating groups as diethylenetriaminepentaacetic acid (DTPA, see Example X, infra) or ethylenediaminetetraacetic acid (EDTA). DTPA, for example, is available as the anhydride, which can readily modify the $NH_2$-containing polypeptides of this invention.

For in vivo diagnosis or therapy, radionuclides may be bound to the polypeptide either directly or indirectly using a chelating agent such as DTPA and EDTA. Examples of such radionuclides are $^{99}$Tc, $^{123}$I, $^{125}$I, $^{131}$I, $^{111}$In, $^{97}$Ru, $^{67}$Cu, $^{67}$Ga, $^{68}$Ga, $^{72}$As, $^{89}$Zr, $^{90}$Y and $^{201}$Tl. Generally, the amount of labeled polypeptide needed for detectability in diagnostic use will vary depending on considerations such as age, condition, sex, and extent of disease in the patient, contraindications, if any, and other variables, and is to be adjusted by the individual physician or diagnostician. Dosage can vary from 0.01 mg/kg to 100 mg/kg.

The polypeptide can also be made detectable by coupling thereto a phosphorescent or a chemiluminescent compound. The presence of the chemiluminescent-tagged polypeptide is then determined by detecting the presence of luminescence that arises during the course of a chemical reaction. Examples of particularly useful chemiluminescers are luminol, isoluminol, theromatic acridinium ester, imidazole, acridinium salt and oxalate ester. Likewise, a bioluminescent compound may be used to label the polypeptides. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In yet another embodiment, colorimetric detection is used, based on chromogenic compounds which have, or result in, chromophores with high extinction coefficients.

In situ detection of the labeled polypeptide may be accomplished by removing a histological specimen from a subject and examining it by microscopy under appropriate conditions to detect the label. Those of ordinary skill will readily perceive that any of a wide variety of histological methods (such as staining procedures) can be modified in order to achieve such in situ detection.

For diagnostic in vivo radioimaging, the type of detection instrument available is a major factor in selecting a radionuclide. The radionuclide chosen must have a type of decay which is detectable by a particular instrument. In general, any conventional method for visualizing diagnostic imaging can be utilized in accordance with this invention. Another factor in selecting a radionuclide for in vivo diagnosis is that its half-life be long enough so that the label is still detectable at the time of maximum uptake by the target tissue, but short enough so that deleterious irradiation of the host is minimized. In one preferred embodiment, a radionuclide used for in vivo imaging does not emit particles, but produces a large number of photons in a 140–200 keV range, which may be readily detected by conventional gamma cameras.

In vivo imaging may be used to detect occult metastases which are not observable by other methods. Imaging could be used to stage tumors non-invasively or to detect other diseases which are associated with the presence of increased levels of a HK-D3-binding site or ligand.

Peptidomimetics

A preferred type of chemical derivative of the polypeptides described herein is a peptidomimetic compound which mimics the biological effects of HK-D3. A peptidomimetic agent may be an unnatural peptide or a non-peptide agent that recreates the stercospatial properties of the binding elements of HK-D3 such that it has the binding activity or biological activity of HK-D3. Similar to biologically active HK-D3 polypeptides, a peptidomimetic will have a binding face (which interacts with any ligand to which HK-D3 binds) and a non-binding face. Again, similar to HK-D3, the non-binding face of a peptidomimetic will contain functional groups which can be modified by various therapeutic and diagnostic moieties without modifying the binding face of the peptidomimetic. A preferred embodiment of a peptidomimetic would contain an aniline on the non-binding face of the molecule. The $NH_2$-group of an aniline has a pKa ~4.5 and could therefore be modified by any $NH_2$— selective reagent without modifying any $NH_2$ functional groups on the binding face of the peptidomimetic. Other peptidomimetics may not have any $NH_2$ functional groups on their binding face and therefore, any $NH_2$, without regard for $pK_a$ could be displayed on the non-binding face as a site for conjugation. In addition other modifiable functional groups, such as —SH and —COOH could be incorporated into the non-binding face of a peptidomimetic as a site of conjugation. A therapeutic or diagnostic moiety could also be directly incorporated during the synthesis of a peptidomimetic and preferentially be displayed on the non-binding face of the molecule.

This invention also includes compounds that retain partial peptide characteristics. For example, any proteolytically unstable bond within a peptide of the invention could be selectively replaced by a non-peptidic element such as an isostere (N-methylation; D-amino acid) or a reduced peptide bond while the rest of the molecule retains its polypeptide nature.

Peptidomimetic compounds, either agonists, substrates or inhibitors, have been described for a number of bioactive polypeptides such as opioid peptides, VIP, thrombin, HIV protease, etc. Methods for designing and preparing peptidomimetic compounds are known in the art (Hruby, V J, *Biopolymers* 33:1073–1082 (1993); Wiley, R A et al., *Med. Res. Rev.* 13:327–384 (1993); Moore et al., *Adv. in Phar-* macol 33:91–141 (1995); Giannis et al., *Adv. in Drug Res.* 29:1–78 (1997), which references are incorporated by reference in their entirety). These methods are used to make peptidomimetics that possess at least the binding capacity and specificity of the HK-D3 polypeptides and preferably also possess the biological activity. Knowledge of peptide chemistry and general organic chemistry available to those skilled in the art are sufficient, in view of the present disclosure, for designing and synthesizing such compounds.

For example, such peptidomimetics may be identified by inspection of the cystallographically-derived three-dimensional structure of a polypeptide of the invention either free or bound in complex with a ligand such as (a) heparin, plasminogen, fibrinogen, vitronectin and thrombospondin or (b) small ligands, such as heme and transition metal ions (zinc, copper and nickel). Alternatively, the structure of a polypeptide of the invention bound to its ligand can be gained by the techniques of nuclear magnetic resonance spectroscopy. The better knowledge of the stereochemistry of the interaction of the polypeptide with its ligand or receptor will permit the rational design of such peptidomimetic agents. The structure of a polypeptide or protein of the invention in the absence of ligand could also provide a scaffold for the design of mimetic molecules.

In Vitro Testing of Compositions

A. Assay for Endothelial Cell Migration

For EC migration, transwells are coated with type I collagen (50 µg/mL) by adding 200 µL of the collagen solution per transwell, then incubating overnight at 37° C. The transwells are assembled in a 24-well plate and a chemoattractant (e.g., FGF-2) is added to the bottom chamber in a total volume of 0.8 mL media. ECs, such as HUVEC, which have been detached from monolayer culture using trypsin, are diluted to a final concentration of about $10^6$ cells/mL with serum-free media and 0.2 mL of this cell suspension is added to the upper chamber of each transwell. Inhibitors to be tested are added to both the upper and lower chambers, and the migration is allowed to proceed for 5 hrs in a humidified atmosphere at 37° C. The transwells are removed from the plate stained using DiffQuik®. Cells which did not migrate are removed from the upper chamber by scraping with a cotton swab and the membranes are detached, mounted on slides, and counted under a high-power field (400×) to determine the number of cells migrated.

B. Biological Assay of Anti-Invasive Activity

The compositions of the invention are tested for their anti-invasive capacity. The ability of cells such as ECs or tumor cells (e.g., PC-3 human prostatic carcinoma) cells to invade through a reconstituted basement membrane (Matrigel®) in an assay known as a Matrigel® invasion assay system as described in detail by Kleinman et al., *Biochemistry* 25: 312–318,1986 and Parish et al., *Int. J. Cancer* 52:378–383,1992. Matrigel® is a reconstituted basement membrane containing type IV collagen, laminin, heparan sulfate proteoglycans such as perlecan, which bind to and localize bFGF, vitronectin as well as transforming growth factor-β (TGFβ), urokinase-type plasminogen activator (uPA), tissue plasminogen activator (tPA), and the serpin known as plasminogen activator inhibitor type 1 (PAI-1) (Chambers et al., *Canc. Res.* 55:1578–1585, 1995). It is accepted in the art that results obtained in this assay for compounds which target extracellular receptors or enzymes are predictive of the efficacy of these compounds in vivo (Rabbani et al., *Int. J. Cancer* 63: 840–845, 1995).

Such assays employ transwell tissue culture inserts. Invasive cells are defined as cells which are able to traverse through the Matrigel® and upper aspect of a polycarbonate membrane and adhere to the bottom of the membrane. Transwells (Costar) containing polycarbonate membranes (8.0 µm pore size) are coated with Matrigel® (Collaborative Research), which has been diluted in sterile PBS to a final concentration of 75 µg/mL (60 µL of diluted Matrigel® per insert), and placed in the wells of a 24-well plate. The membranes are dried overnight in a biological safety cabinet, then rehydrated by adding 100 µL of DMEM containing antibiotics for 1 hour on a shaker table. The DMEM is removed from each insert by aspiration and 0.8 mL of DMEM supplemented with 10% fetal bovine serum (FBS) and antibiotics is added to each well of the 24well plate such that it surrounds the outside of the transwell ("lower chamber"). Fresh DMEM/antibiotics (100 µL), human Glu-plasminogen (5 µg/mL), and any inhibitors to be tested are added to the top, inside of the transwell ("upper chamber"). The cells which are to be tested are trypsinized and resuspended in DMEM/antibiotics, then added to the top chamber of the transwell at a final concentration of 800,000 cells/ML. The final volume of the upper chamber is adjusted to 200 µL. The assembled plate is then incubated in a humid 5% $CO_2$ atmosphere for 72 hours. After incubation, the cells are fixed and stained using DiffQuik® (Giemsa stain) and the upper chamber is then scraped using a cotton swab to remove the Matrigel® and any cells which did not invade through the membrane. The membranes are detached from the transwell using an X-acto® blade, mounted on slides using Permount® and cover-slips, then counted under a high-powered (400×) field. An average of the cells invaded is determined from 5–10 fields counted and plotted as a function of inhibitor concentration.

C. Tube-Formation Assays of Anti-Angiogenic Activity

The compounds of this invention are tested for their anti-angiogenic activity in one of two different assay systems in vitro.

Endothelial cells, for example, HUVEC or human microvascular endothelial cells (HMVEC) which can be prepared or obtained commercially, are mixed at a concentration of $2 \times 10^5$ cells/mL with fibrinogen (5 mg/mL in phosphate buffered saline (PBS) in a 1:1 (v/v) ratio. Thrombin is added (5 units/mL final concentration) and the mixture is immediately transferred to a 24-well plate (0.5 mL per well). The fibrin gel is allowed to form and then VEGF and bFGF are added to the wells (each at 5 ng/mL final concentration) along with the test compound. The cells are incubated at 37° C. in 5% $CO_2$ for 4 days at which time the cells in each well are counted and classified as either rounded, elongated with no branches, elongated with one branch, or elongated with 2 or more branches. Results are expressed as the average of 5 different wells for each concentration of compound. Typically, in the presence of angiogenic inhibitors, cells remain either rounded or form undifferentiated tubes (e.g. 0 or 1 branch).

This assay is recognized in the art to be predictive of angiogenic (or anti-angiogenic) efficacy in vivo (Min, H Y et al., *Cancer Res.* 56: 2428–2433, 1996).

In an alternate assay, endothelial cell tube formation is observed when endothelial cells are cultured on Matrigel® (Schnaper et al., *J. Cell. Physiol.* 165:107–118 1995). Endothelial cells ($1 \times 10^4$ cells/well) are transferred onto Matrigel®-coated 24-well plates, and tube formation is quantitated after 48 hrs. Inhibitors are tested by adding them either at the same time as the endothelial cells or at various time points thereafter. Tube formation can also be stimulated by adding (a) angiogenic growth factors such as bFGF or VEGF, (b) differentiation stimulating agents (e.g., PMA) or (c) a combination of these.

This assay models angiogenesis by presenting to the endothelial cells a particular type of basement membrane, namely the layer of matrix which migrating and differentiating endothelial cells might be expected to first encounter. In addition to bound growth factors, the matrix components found in Matrigel® (and in basement membranes in situ) or proteolytic products thereof may also be stimulatory for endothelial cell tube formation which makes this model complementary to the fibrin gel angiogenesis model previously described (Blood et at., *Biochim. Biophys. Acta* 1032: 89–118, 1990; Odedra et al., *Pharmac. Ther.* 49:111–124, 1991). The compounds of this invention inhibit endothelial cell tube formation in both assays, which suggests that the compounds will also have anti-angiogenic activity.

D. Assays for the Inhibition of Proliferation

The ability of the compounds of the invention to inhibit the proliferation of EC's may be determined in a 96-well format. Type I collagen (gelatin) is used to coat the wells of the plate (0.1–1 mg/mL in PBS, 0.1 mL per well for 30 minutes at room temperature). After washing the plate (3× w/PBS), 3–6,000 cells are plated per well and allowed to attach for 4 hrs (37° C/5% $CO_2$) in Endothelial Growth Medium (EGM; Clonetics ) or M199 media containing 0.1–2% FBS. The media and any unattached cells are removed at the end of 4 hrs and fresh media containing bFGF (1–10 ng/mL) or VEGF (1–10 ng/mL) is added to each well. Compounds to be tested are added last and the plate is allowed to incubate (37° C./5% $CO_2$) for 24–48 hrs. MTS [(3-(4,5-dimethylthiazol-2-yl)-5-(3-carboxymethoxyphenyl)-2-(4-sulfophenyl)-2H-tetrazolium] (Promega) is added to each well and allowed to incubate from 1–4 hrs. The absorbance at 490 nm, which is proportional to the cell number, is then measured to determine the differences in proliferation between control wells and those containing test compounds.

A similar assay system can be set up with cultured adherent tumor cells. However, collagen may be omitted in this format. Tumor cells (e.g., 3,000–10,000/well) are plated and allowed to attach overnight. Serum free medium is then added to the wells, and the cells are synchronized for 24 hrs. Medium containing 10% FBS is then added to each well to stimulate proliferation. Compounds to be tested are included in some of the wells. After 24 hrs, MTS is added to the plate and the assay developed and read as described above.

E. Assays of Cytotoxicity

The anti-proliferative and cytotoxic effects of the compositions may be determined for various cell types including tumor cells, ECs, fibroblasts and macrophages. This is especially useful when testing a compound of the invention which has been conjugated to a therapeutic moiety such as a radiotherapeutic or a toxin. For example, a conjugate of one of the compositions with Bolton-Hunter reagent which has been iodinated with $^{131}I$ would be expected to inhibit the proliferation of cells expressing an HK-D3 binding site/receptor (most likely by inducing apoptosis). Anti-proliferative effects would be expected against tumor cells and stimulated endothelial cells but, under some circumstances not quiescent endothelial cells or normal human dermal fibroblasts. Any anti-proliferative or cytotoxic effects observed in the normal cells would represent non-specific toxicity of the conjugate.

A typical assay would involve plating cells at a density of $5–10×10^3$ cells per well in a 96-well plate. The compound to be tested is added at a concentration 10× the $IC_{50}$ measured in a binding assay (this will vary depending on the conjugate) and allowed to incubate with the cells for 30 minutes. The cells are washed 3 times X with media, then fresh medium containing [$^3H$]thymidine (0.5–1 µCi) is added to the cells, and they are allowed to incubate at 37° C. in 5% $CO_2$ (or other appropriate atmosphere) for 24 and 48 hours. Cells are lysed at the various time points using, for example, 1 M NaOH and counts per well determined using a liquid scintillation counter. Proliferation may be measured non-radioactively using MTS reagent or CyQuant® to measure total cell number. For cytotoxicity assays (measuring cell lysis), a Promega 96-well cytotoxicity kit is used. If there is evidence of anti-proliferative activity, induction of apoptosis may be measured using TumorTACS (Genzyme).

Caspase-3 Activity

The ability of the compounds of the invention to promote apoptosis of EC's may be determined by measuring activation of caspase-3. Type I collagen (gelatin) is used to coat a P100 plate and $5×10^5$ ECs are seeded in EGM containing 10% FBS. After 24 hours (at 37° C. in 5% $CO_2$) the medium is replaced by EGM containing 2% FBS, 10 ng/ml bFGF and the desired test compound. The cells are harvested after 6 hours, cell lysates prepared in 1% Triton and assayed using the EnzChek®Caspase-3 Assay Kit #1 (Molecular Probes) according to the manufactures' instructions.

In Vivo Study of the HK-D3 Polypeptides

A. Corneal Angiogenesis Model

The protocol used is essentially identical to that described by Volpert et al. (*J. Clin. Invest.* 98:671–679 (1996)). Briefly, female Fischer rats (120–140 gms) are anesthetized and pellets (5 µl) comprised of Hydron®, bFGF (150 nM), and the compounds to be tested are implanted into tiny incisions made in the cornea 1.0–1.5 mm from the limbus. Neovascularization is assessed at 5 and 7 days after implantation. On day 7, animals are anesthetized and infused with a dye such as colloidal carbon to stain the vessels. The animals are then euthanized, the corneas fixed with formalin, and the corneas flattened and photographed to assess the degree of neovascularization. Neovessels may be quantitated by imaging the total vessel area or length or simply by counting vessels.

B. Matrigl® Plus Assay

This assay is performed essentially as described by Passaniti et al. (*Lab Invest.* 67:519–528 (1992). Ice-cold Matrigel® (e.g., 500 µL) (Collaborative Biomedical Products, Inc., Bedford, Mass.) is mixed with heparin (e.g., 50 µg/ml), FGF-2 (e.g., 400 ng/ml) and the compound to be tested. In some assays, bFGF may be substituted with tumor cells as the angiogenic stimulus. The Matrigel® mixture is injected subcutaneously into 4–8 week-old athymic nude mice at sites near the abdominal midline, preferably 3 injections per mouse. The injected Matrigel® forms a palpable solid gel. Injection sites are chosen such that each animal receives a positive control plug (such as FGF-2+heparin), a negative control plug (e.g., buffer+heparin) and a plug that includes the compound being tested for its effect on angiogenesis, e.g., (FGF-2+heparin+compound). All treatments are preferably run in triplicate. Animals are sacrificed by cervical dislocation at about 7 days post injection or another time that may be optimal for observing angiogenesis. The mouse skin is detached along the abdominal midline, and the Matrigel® plugs are recovered and scanned immediately at high resolution. Plugs are then dispersed in water and incubated at 37° C. overnight. Hemoglobin (Hb) levels are determined using Drabkin's solution (e.g., obtained from Sigma) according to the manufacturers' instructions. The amount of Hb in the plug is an indirect measure of angiogenesis as it reflects the amount of blood in the sample. In addition, or alternatively, animals may be injected prior to sacrifice with a 0.1 ml buffer (preferably PBS) containing a high molecular weight dextran to which is conjugated a fluorophore. The amount of fluorescence in the dispersed plug, determined fluorimetrically, also serves as a measure of angiogenesis in the plug. Staining with mAb anti-CD31 (CD31 is "platelet-endothelial cell adhesion molecule or PECAM") may also be used to confirm neovessel formation and microvessel density in the plugs.

C. Chick Chorioallantoic Membrane (CAM) Angiogenesis Assay

This assay is performed essentially as described by Nguyen et al. (*Microvascular Res.* 47:31–40 (1994)). A mesh containing either angiogenic factors (bFGF) or tumor cells plus inhibitors is placed onto the CAM of an 8-day old chick embryo and the CAM observed for 3–9 days after implantation of the sample. Angiogenesis is quantitated by determining the percentage of squares in the mesh which contain blood vessels.

D. In Vivo Assessment Angiogenesis Inhibition and Anti-Tumor Effects Using the Matrigel® Plug Assay with Tumor Cells In this assay, tumor cells, for example 1–5×10$^6$ cells of the 3LL Lewis lung carcinoma or the rat prostate cell line MatLyLu ("MLL"), are mixed with Matrigel® and then injected into the flank of a mouse following the protocol described in Sec. B., above. A mass of tumor cells and a powerful angiogenic response can be observed in the plugs after about 5 to 7 days. The anti-tumor and anti-angiogenic action of a compound in an actual tumor environment can be evaluated by including it in the plug. Measurement is then made of tumor weight, Hb levels or fluorescence levels (of a dextran-fluorophore conjugate injected prior to sacrifice). To measure Hb or fluorescence, the plugs are first homogenize with a tissue homogenizer.

E. Xenograft Model of Subcutaneous (s.c.) Tumor Growth

Nude mice are inoculated with MDA-MB-231 cells (human breast carcinoma) and Matrigel® (1×10$^6$ cells in 0.2 mL) s.c. in the right flank of the animals. The tumors are staged to 200 mm$^3$ and then treatment with a test composition is initiated (100 µg/animal/day given q.d. IP). Tumor volumes are obtained every other day and the animals are sacrificed after 2 weeks of treatment. The tumors are excised, weighed and paraffin embedded. Histological sections of the tumors are analyzed by H and E, anti-CD31, Ki-67, TUNEL, and CD68 staining.

F. Xenograft Model of Metastasis

The compounds of this invention are also tested for inhibition of late metastasis using an experimental metastasis model (Crowley, C W et al., *Proc. Natl. Acad. Sci. USA* 90 5021–5025 (1993)). Late metastasis involves the steps of attachment and extravasation of tumor cells, local invasion, seeding, proliferation and angiogenesis. Human prostatic carcinoma cells (PC-3) transfected with a reporter gene, preferably the green fluorescent protein (GFP) gene, but as an alternative with a gene encoding the enzymes chloramphenicol acetyl-transferase (CAT), luciferase or LacZ, are inoculated into nude mice. This approach permits utilization of either of these markers (fluorescence detection of GFP or histochemical colorimetric detection of enzymatic activity) to follow the fate of these cells. Cells are injected, preferably iv, and metastases identified after about 14 days, particularly in the lungs but also in regional lymph nodes, femurs and brain. This mimics the organ tropism of naturally occurring metastases in human prostate cancer. For example, GFP-expressing PC-3 cells (1×10$^6$ cells per mouse) are injected iv into the tail veins of nude (nu/nu) mice. Animals are treated with a test composition at 100 µg/animal/day given q.d. IP. Single metastatic cells and foci are visualized and quantitated by fluorescence microscopy or light microscopic histochemistry or by grinding the tissue and quantitative colorimetric assay of the detectable label.

G. Inhibition of Spontaneous Metastasis In Vivo by HK-D3 and Functional Derivatives The rat syngeneic breast cancer system-(Xing et al., *Int. J. Cancer* 67:423–429 (1996) employs Mat BIII rat breast cancer cells. Tumor cells, for example about 10$^6$ suspended in 0.1 mL PBS, are inoculated into the mammary fat pads of female Fisher rats. At the time of inoculation, a 14-day Alza osmotic mini-pump is implanted intraperitoneally to dispense the test compound. The compound is dissolved in PBS (e.g., 200 mM stock), sterile filtered and placed in the minipump to achieve a release rate of about 4 mg/kg/day. Control animals receive vehicle (PBS) alone or a vehicle control polypeptide in the minipump. Animals are sacrificed at about day 14.

Therapeutic Outcomes

In the rats treated with the active peptide/polypeptide compounds of the present invention, significant reductions in the size of the primary tumor and in the number of metastases in the spleen, lungs, liver, kidney and lymph nodes (enumerated as discrete foci) are observed. Histological and immunohistochemical analysis reveal increased necrosis and signs of apoptosis in tumors in treated animals. Large necrotic areas are seen in tumor regions lacking neovascularization as a result of this treatment. HK-D3 or its derivative, to which $^{131}$I is conjugated (either 1 or 2 1 atoms per molecule of polypeptide) are effective radiotherapeutics and are found to be at least two-fold more potent than the unconjugated polypeptides. In contrast, treatment with control polypeptides fails to cause a significant change in tumor size or metastasis.

H. 3LL Lewis Lung Carcinoma: Primary Tumor Growth

This tumor line arose spontaneously in 1951 as carcinoma of the lung in a C57BL/6 mouse (*Cancer Res* 15:39, 1955. See, also Malave, I. et al., *J. Nat'l. Canc. Inst.* 62:83–88 (1979)). It is propagated by passage in C57BL/6 mice by subcutaneous (sc) inoculation and is tested in semiallogeneic C57BL/6×DBA/2 F$_1$ mice or in allogeneic C3H mice. Typically six animals per group for subcutaneously (sc) implant, or ten for intramuscular (im) implant are used. Tumor may be implanted sc as a 2–4 mm fragment, or im or sc as an inoculum of suspended cells of about 0.5–2×10$^6$ cells. Treatment begins about 24 hours after implant or is delayed until a tumor of specified size (usually approximately 400 mg) can be palpated. The test compound is administered ip daily for 11 days Animals are followed by weighing, palpation, and measurement of tumor size. Typical tumor weight in untreated control recipients on day 12 after im inoculation is 500–2500 mg. Typical median survival time is 18–28 days.

A positive control compound, for example cyclophosphamide at 20 mg/kg/injection per day on days 1–11 is used. Results computed include mean animal weight, tumor size, tumor weight, survival time. For confirmed therapeutic activity, the test composition should be tested in two multi-dose assays.

I. 3LL Lewis Lung Carcinoma: Primary Growth and Metastasis Model

This model has been utilized by a number of investigators. See, for example, Gorelik, E. et al., *J. Nat'l. Canc. Inst.* 65:1257–1264 (1980); Gorelik, E. et al., *Rec. Results Canc. Res.* 75:20–28 (1980); Isakov, N. et al., *Invasion Metas.* 2:12–32 (1982); Talmadge J E et al., *J. Nat'l. Canc. Inst.* 69:975–980 (1982); Hilgard, P. et al., *Br. J. Cancer* 35:78–86(1977)). Test mice are male C57BL/6 mice, 2–3 months old. Following sc, im, or intra-footpad implantation, this tumor produces metastases, preferentially in the lungs. With some lines of the tumor, the primary tumor exerts anti-metastatic effects and must first be excised before study of the metastatic phase (see also U.S. Pat. No. 5,639,725).

Single-cell suspensions are prepared from solid tumors by treating minced tumor tissue with a solution of 0.3% trypsin. Cells are washed 3 times with PBS (pH 7.4) and suspended in PBS. Viability of the 3LL cells prepared in this way is generally about 95–99% (by trypan blue dye exclusion). Viable tumor cells (e.g., $3 \times 10^{4-5 \times 10^6}$) suspended in 0.05 ml PBS are injected subcutaneously, either in the dorsal region or into one hind foot pad of C57BL/6 mice. Visible tumors appear after 3–4 days after dorsal sc injection of $10^6$ cells. The day of tumor appearance and the diameters of established tumors are measured by caliper every two days.

The treatment is given as one or two doses of polypeptide or derivative, per week. In another embodiment, the polypeptide is delivered by osmotic minipump.

In experiments involving tumor excision of dorsal tumors, when tumors reach about 1500 mm$^3$ in size, mice are randomized into two groups: (1) primary tumor is completely excised; or (2) sham surgery is performed and the tumor is left intact. Although tumors from 500–3000 mm$^3$ inhibit growth of metastases, 1500 mm$^3$ is the largest size primary tumor that can be safely resected with high survival and without local regrowth. After 21 days, all mice are sacrificed and autopsied.

Lungs are removed and weighed. Lungs are fixed in Bouin's solution and the number of visible metastases is recorded. The diameters of the metastases are also measured using a binocular stereoscope equipped with a micrometer-containing ocular under 8× magnification. On the basis of the recorded diameters, it is possible to calculate the volume of each metastasis. To determine the total volume of metastases per lung, the mean number of visible metastases is multiplied by the mean volume of metastases. To further determine metastatic growth, it is possible to measure incorporation of $^{125}$IdUrd into lung cells (Thakur, M L et al., *J. Lab. Clin. Med.* 89:217–228 (1977)). Ten days following tumor amputation, 25 µg of fluorodeoxyuridine is inoculated into the peritoneums of tumor-bearing (and, if used, tumor-resected mice). After 30 min, mice are given 1 µCi of $^{125}$IdUrd (iododeoxyuridine). One day later, lungs and spleens are removed and weighed, and a degree of $^{125}$IdUrd incorporation is measured using a gamma counter.

In mice with footpad tumors, when tumors reach about 8–10 mm in diameter, mice are randomized into two groups: (1) legs with tumors are amputated after ligation above the knee joints; or (2) mice are left intact as nonamputated tumor-bearing controls. (Amputation of a tumor-free leg in a tumor-bearing mouse has no known effect on subsequent metastasis, ruling out possible effects of anesthesia, stress or surgery). Mice are killed 10–14 days after amputation. Metastases are evaluated as described above.

Statistics: Values representing the incidence of metastases and their growth in the lungs of tumor-bearing mice are generally not normally distributed. Therefore, non-parametric statistics such as the Mann-Whitney U-Test may be used for analysis.

Study of this model by Gorelik et al. (1980, supra) showed that the size of the tumor cell inoculum determined the extent of metastatic growth. The rate of metastasis in the lungs of operated mice was different from primary tumor-bearing mice. Thus in the lungs of mice in which the primary tumor had been induced by inoculation of larger doses of 3LL cells (1–5×$10^6$) followed by surgical removal, the number of metastases was lower than that in nonoperated tumor-bearing mice, though the volume of metastases was higher than in the nonoperated controls. Using $^{125}$IdUrd incorporation as a measure of lung metastasis, no significant differences were found between the lungs of tumor-excised mice and tumor-bearing mice originally inoculated with $10^6$ 3LL cells. Amputation of tumors produced following inoculation of $10^5$ tumor cells dramatically accelerated metastatic growth. These results were in accord with the survival of mice after excision of local tumors. The phenomenon of acceleration of metastatic growth following excision of local tumors had been repeatedly observed (for example, see U.S. Pat. No. 5,639,725). These observations have implications for the prognosis of patients who undergo cancer surgery.

For a compound to be useful in accordance with this invention, it should demonstrate activity in at least one of the above (in vitro or in vivo) assay systems.

Pharmaceutical and Therapeutic Compositions and Their Administration

The compounds that may be employed in the pharmaceutical compositions of the invention include all of the polypeptide compounds described above, as well as the pharmaceutically acceptable salts of these compounds. Pharmaceutically acceptable acid addition salts of the compounds of the invention containing a basic group are formed where appropriate with strong or moderately strong, non-toxic, organic or inorganic acids by methods known to the art. Exemplary of the acid addition salts that are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

Pharmaceutically acceptable base addition salts of compounds of the invention containing an acidic group are prepared by known methods from organic and inorganic bases and include, for example, nontoxic alkali metal and alkaline earth bases, such as calcium, sodium, potassium and ammonium hydroxide; and nontoxic organic bases such as triethylamine, butylamine, piperazine, and tri(hydroxymethyl)methylamine.

As stated above, the compounds of the invention possess the ability to inhibit endothelial cell proliferation, motility, or invasiveness and angiogenesis, properties that are exploited in the treatment of cancer, in particular metastatic cancer. A composition of this invention may be active per se, or may act as a "pro-drug" that is converted in vivo to the active form.

Therapeutically Labeled Compositions

In a preferred embodiment, the polypeptide described herein are "therapeutically conjugated" or "therapeutically labeled" (terms which are intended to be interchangeable)

and used to deliver a therapeutic agent to the site to which the compounds home and bind, such as sites of tumor metastasis or foci of infection/inflammation, restenosis or fibrosis. The term "therapeutically conjugated" means that the modified polypeptide is conjugated to another therapeutic agent that is directed either to the underlying cause or to a "component" of tumor invasion, angiogenesis, inflammation or other pathology. A therapeutically labeled polypeptide carries a suitable therapeutic "label" also referred to herein as a "therapeutic moiety." A therapeutic moiety is an atom, a molecule, a compound or any chemical component added to the polypeptide that renders it active in treating a target disease or condition, primarily one a associated with undesired angiogenesis. As noted above, the polypeptides of the present invention are prepared by conventional biochemical or recombinant means. The therapeutic moiety may be bound directly or indirectly to the polypeptide. The therapeutically labeled polypeptide is administered as pharmaceutical composition which comprises a pharmaceutically acceptable carrier or excipient, and is preferably in a form suitable for injection.

Examples of useful therapeutic radioisotopes (ordered by atomic number) include $^{47}$Sc, $^{67}$Cu, $^{90}$Y, $^{109}$Pd, $^{125}$I, $^{131}$I, $^{186}$Re, $^{188}$Re, $^{199}$Au, $^{211}$At, $^{212}$Pd and $^{217}$Bi. These atoms can be conjugated to the polypeptide directly, indirectly as part of a chelate, or, in the case of iodine, indirectly as part of an iodinated Bolton-Hunter group. The radioiodine can be introduced either before or after this group is coupled to the polypeptide compound.

Preferred doses of the radionuclide conjugates are a fiction of the specific radioactivity to be delivered to the target site which varies with tumor type, tumor location and vascularization, kinetics and biodistribution of the polypeptide carrier, energy of radioactive emission by the nuclide, etc. Those skilled in the art of radiotherapy can readily adjust the dose of the polypeptide in conjunction with the dose of the particular nuclide to effect the desired therapeutic benefit without undue experimentation.

Another therapeutic approach included here is the use of boron neutron capture therapy, where a boronated polypeptide is delivered to a desired target site, such as a tumor, most preferably an intracranial tumor (Barth, R F, *Cancer Invest.* 14:534–550 (1996); Mishima, Y. (ed.), *Cancer Neutron Capture Therapy*, New York: Plenum Publishing Corp., 1996; Soloway, A H et al., (eds), *J. Neuro-Oncol.* 33:1–188 (1997). The stable isotope $^{10}$B is irradiated with low energy (<0.025 eV) thermal neutrons, and the resulting nuclear capture yields α-particles and $^{7}$Li nuclei which have high linear energy transfer and respective path lengths of about 9 and 5 μm. This method is predicated on $^{10}$B accumulation in the tumor with lower levels in blood, endothelial cells and normal tissue (e.g., brain). Such delivery has been accomplished using epidermal growth factor (Yang. W. et al., *Cancer Res* 57:4333–4339 (1997).

Other therapeutic agents which can be coupled to the polypeptide compounds according to the method of the invention are drugs, prodrugs, enzymes for activating prodrugs, photosensitizing agents, nucleic acid therapeutics, antisense vectors, viral vectors, lectins and other toxins.

Lectins are proteins, commonly derived from plants, that bind to carbohydrates. Among other activities, some lectins are toxic. Some of the most cytotoxic substances known are protein toxins of bacterial and plant origin (Frankel, A E et al., Ann. Rev. Med. 37:125–142 (1986)). These molecules binding the cell surface and inhibit cellular protein synthesis. The most commonly used plant toxins are ricin and abrin; the most commonly used bacterial toxins are diphtheria toxin and Pseudomonas exotoxin A. In ricin and abrin, the binding and toxic functions are contained in two separate protein subunits, the A and B chains. The ricin B chain binds to the cell surface carbohydrates and promotes the uptake of the A chain into the cell. Once inside the cell, the ricin A chain inhibits protein synthesis by inactivating the 60S subunit of the eukaryotic ribosome (Endo, Y. et al., J. Biol. Chem. 262: 5908–5912 (1987)). Other plant derived toxins, which are single chain ribosomal inhibitory proteins, include pokeweed antiviral protein, wheat germ protein, gelonin, dianthins, momorcharins, trichosanthin, and many others (Strip, F. et al., FEBS Lett. 195:1–8 (1986)). Diphtheria toxin and Pseudomonas exotoxin A are also single chain proteins, and their binding and toxicity functions reside in separate domains of the same protein Pseudomonas exotoxin A has the same catalytic activity as diphtheria toxin. Ricin has been used therapeutically by binding its toxic α-chain, to targeting molecules such as antibodies to enable site-specific delivery of the toxic effect. Bacterial toxins have also been used as anti-tumor conjugates. As intended herein, a toxic peptide chain or domain is conjugated to a compound of this invention and delivered in a site-specific manner to a target site where the toxic activity is desired, such as a metastatic focus. Conjugation of toxins to protein such as antibodies or other ligands are known in the art (Olsnes, S. et al., Immunol. Today 10:291–295 (1989); Vitetta, E S et al., Ann. Rev. Immunol. 3:197–212 (1985)).

Cytotoxic drugs that interfere with critical cellular processes including DNA, RNA, and protein synthesis, have been conjugated to antibodies and subsequently used for in vivo therapy. Such drugs, including, but not limited to, daunorubicin, doxorubicin, methotrexate, and Mitomycin C are also coupled to the compounds of this invention and used therapeutically in this form.

The compounds of the invention, as well as the pharmaceutically acceptable salts thereof, may be incorporated into convenient dosage forms, such as capsules, impregnated wafers, tablets or injectable preparations. Solid or liquid pharmaceutically acceptable carriers may be employed.

Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline, water, dextrose, glycerol and the like. Similarly, the carrier or diluent may include any prolonged release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., a solution), such as an ampoule, or an aqueous or nonaqueous liquid suspension. A summary of such pharmaceutical compositions may be found, for example, in *Remington's Pharmaceutical Sciences*, Mack Publishing Company, Easton Pa. (Gennaro 18th ed. 1990).

The pharmaceutical preparations are made following conventional techniques of pharmaceutical chemistry involving such steps as mixing, granulating and compressing, when necessary for tablet forms, or mixing, filling and dissolving the ingredients, as appropriate, to give the desired products for oral, parenteral, topical, transdermal, intravaginal, intrapenile, intranasal, intrabronchial, intracranial, intraocular, intraaural and rectal administration. The pharmaceutical compositions may also contain minor amounts of nontoxic auxiliary substances such as wetting or emulsifying agents, pH buffering agents and so forth.

The present invention may be used in the diagnosis or treatment of any of a number of animal genera and species, and are equally applicable in the practice of human or veterinary medicine. Thus, the pharmaceutical compositions can be used to treat domestic and commercial animals, including birds and more preferably mammals, as well as humans.

The term "systemic administration" refers to administration of a composition or agent such as the polypeptide or nucleic acids described herein, in a manner that results in the introduction of the composition into the subject's circulatory system or otherwise permits its spread throughout the body, such as intravenous (i.v.) injection or infusion. "Regional" administration refers to administration into a specific, and somewhat more limited, anatomical space, such as intraperitoneal, intrathecal, subdural, or to a specific organ. Examples include intravaginal, intrapenile, intranasal intrabronchial(or lung instillation), intracranial, intra-aural or intraocular. The term "local administration" refers to administration of a composition or drug into a limited, or circumscribed, anatomic space, such as intratumoral injection into a tumor mass, subcutaneous (s.c.) injections, intramuscular (i.m.) injections. One of skill in the art would understand that local administration or regional administration often also result in entry of a composition into the circulatory system, i.e., so that s.c. or i.m. are also routes for systemic administration. Injectables or infusible preparations can be prepared in conventional forms, either as solutions or suspensions, solid forms suitable for solution or suspension in liquid prior to injection or infusion, or as emulsions. Though the preferred routes of administration are systemic, such as i.v., the pharmaceutical composition may be administered topically or transdermally, e.g., as an ointment, cream or gel; orally, rectally; e.g., as a suppository.

For topical application, the compound may be incorporated into topically applied vehicles such as a salve or ointment. The carrier for the active ingredient may be either in sprayable or nonsprayable form. Non-sprayable forms can be semi-solid or solid forms comprising a carrier indigenous to topical application and having a dynamic viscosity preferably greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Preferred vehicles for non-sprayable topical preparations include ointment bases, e.g., polyethylene glycol-1000 (PEG-1000); conventional creams such as HEB cream; gels; as well as petroleum jelly and the like.

Also suitable for topic application as well as for lung instillation are sprayable aerosol preparations wherein the compound, preferably in combination with a solid or liquid inert carrier material, is packaged in a squeeze bottle or in admixture with a pressurized volatile, normally gaseous propellant. The aerosol preparations can contain solvents, buffers, surfactants, perfumes, and/or antioxidants in addition to the compounds of the invention.

For the preferred topical applications, especially for humans, it is preferred to administer an effective amount of the compound to an affected area, e.g., skin surface, mucous membrane, eyes, etc. This amount will generally range from about 0.001 mg to about 1 g per application, depending upon the area to be treated, the severity of the symptoms, and the nature of the topical vehicle employed.

Other pharmaceutically acceptable carriers for polypeptide or nucleic acid compositions of the present invention are liposomes, pharmaceutical compositions in which the active protein is contained either dispersed or variously present in corpuscles consisting of aqueous concentric layers adherent to lipidic layers. The active polypeptide, or the nucleic acid is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature. Those skilled in the art will appreciate other suitable embodiments of the present liposomal formulations.

Therapeutic compositions for treating tumors and cancer may comprise, in addition to the polypeptide, one or more additional anti-tumor agents, such as mitotic inhibitors, e.g., vinblastine; alkylating agents, e.g., cyclophosphamide; folate inhibitors, e.g., methotrexate, piritrexim or trimetrexate; antimetabolites, e.g., 5-fluorouracil and cytosine arabinoside; intercalating antibiotics, e.g., adriamycin and bleomycin; enzymes or enzyme inhibitors, e.g., asparaginase, topoisomerase inhibitors such as etoposide; or biological response modifiers, e.g., interferons or interleukins. In fact, pharmaceutical compositions comprising any known cancer therapeutic in combination with the polypeptides disclosed herein are within the scope of this invention. The pharmaceutical composition may also comprise one or more other medicaments to treat additional symptoms for which the target patients are at risk, for example, anti-infectives including antibacterial, anti-fungal, anti-parasitic, anti-viral, and anti-coccidial agents.

The therapeutic dosage administered is an amount which is therapeutically effective, as is known to or readily ascertainable by those skilled in the art. The dose is also dependent upon the age, health, and weight of the recipient, kind of concurrent treatment(s), if any, the frequency of treatment, and the nature of the effect desired, such as, for example, anti-inflammatory effects or anti-bacterial effect.

Therapeutic Methods

The methods of this invention may be used to inhibit tumor growth and invasion in a subject or to suppress angiogenesis induced by tumors by inhibiting endothelial cell growth and migration. By inhibiting the growth or invasion of a tumor or angiogenesis, the methods result in inhibition of tumor metastasis. A vertebrate subject, preferably a mammal, more preferably a human, is administered an amount of the compound effective to inhibit tumor growth, invasion or angiogenesis. The compound or pharmaceutically acceptable salt thereof is preferably administered in the form of a pharmaceutical composition as described above.

Doses of polypeptides preferably include pharmaceutical dosage units comprising an effective amount of the polypeptide. Dosage unit form refers to physically discrete units suited as unitary dosages for a mammalian subject; each unit contains a predetermined quantity of active material (e.g., the HK-D3 polypeptide, or nucleic acid encoding the polypeptide) calculated to produce the desired therapeutic effect, in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active compound for the treatment of, and sensitivity of, individual subjects By an effective amount is meant an amount sufficient to achieve a steady state concentration in vivo which results in a measurable reduction in any relevant parameter of disease and may include growth of primary or metastatic tumor, any accepted index of antiangiogenic or anti-proliferative, or apoptosis-inducing reactivity, or a measurable prolongation of disease-free interval or of survival. For example, a reduction in tumor growth in 20% of patients is considered efficacious (Frei III, E., *The Cancer Journal* 3:127–136 (1997)). However, an effect of this magnitude is not considered to be a minimal requirement for the dose to be effective in accordance with this invention.

In one embodiment, an effective dose is preferably 10-fold and more preferably 100-fold higher than the 50% effective dose ($ED_{50}$) of the compound in an in vivo assay as described herein.

The amount of active compound to be administered depends on the precise polypeptide or derivative selected, the disease or condition, the route of administration, the health and weight of the recipient, the existence of other concurrent treatment, if any, the frequency of treatment, the nature of the effect desired, for example, inhibition of tumor metastasis, and the judgment of the skilled practitioner.

A preferred dose for treating a subject, preferably mammalian, more preferably human, with a tumor is an amount of up to about 100 mg of active polypeptide-based compound per kilogram of body weight. A typical single dosage of the polypeptide or peptidomimetic is between about 1 ng and about 100 mg/kg body weight. For topical administration, dosages in the range of about 0.01–20% concentration (by weight) of the compound, preferably 1–5%, are suggested. A total daily dosage in the range of about 0.1 milligrams to about 7 grams is preferred for intravenous administration. The foregoing ranges are, however, suggestive, as the number of variables in an individual treatment regime is large, and considerable excursions from these preferred values are expected.

An effective amount or dose of the polypeptide for inhibiting endothelial cell proliferation or migration in vitro is in the range of about 1 picogram to about 5 nanograms per cell. Effective doses and optimal dose ranges may be determined in vitro using the methods described herein.

The compounds of the invention may be characterized as producing an inhibitory effect on tumor cell or endothelial cell proliferation, migration, invasion, or on angiogenesis, on tumor metastasis or on inflammatory reactions. The compounds are especially useful in producing an anti-tumor effect in a mammalian host, preferably human, harboring a tumor.

Angiogenesis inhibitors may play a role in preventing or ameliorating inflammatory angiogenesis and gliosis following traumatic spinal cord injury, thereby promoting the reestablishment of neuronal connectivity (Wamil, A W et al., *Proc. Nat'l. Acad. Sci. USA* 95:13188–13193 (1998)). Therefore, the compositions of the present invention are administered as soon as possible after traumatic spinal cord injury and for several days up to about two weeks thereafter to inhibit the angiogenesis and gliosis that would sterically prevent reestablishment of neuronal connectivity. The treatment reduces the area of damage at the site of spinal cord injury and facilitates regeneration of neuronal function and thereby prevents paralysis. The compounds of the invention are expected also to protect axons from Wallerian degeneration, reverse aminobutyrate-mediated depolarization (occurring in traumatized neurons), and improve recovery of neuronal conductivity of isolated central nervous system cells and tissue in culture.

General Recombinant DNA Methods

Basic texts disclosing general methods of molecular biology, all of which are incorporated by reference, include:

Sambrook, J et al., *Molecular Cloning: A Laboratory Manual,* 2nd (or later) Edition, Cold Spring Harbor Press, Cold Spring Harbor, N.Y., 1989; Ausubel, F M et al. *Current Protocols in Molecular Biology,* Vol. 2, Wiley-Interscience, New York, (current edition); Kriegler, *Gene Transfer and Expression: A Laboratory Manual* (1990); Glover, D M, editor, *DNA Cloning: A Practical Approach,* vol. I & II, IRL Press, 1985; Albers, B. et al., *Molecular Biology of the Cell,* 2nd (or later) Ed., Garland Publishing, Inc., New York, N.Y. (1989); Watson, J D et al., *Recombinant DNA,* 2nd (or later) Ed., Scientific American Books, New York, 1992; and Old, R W et al., *Principles of Gene Manipulation: An Introduction to Genetic Engineering,* 2nd (or later) Ed., University of California Press, Berkeley, Calif. (1981).

Unless otherwise indicated, a particular nucleic acid sequence is intended to encompasses conservative substitution variants thereof (e.g., degenerate codon substitutions) and a complementary sequence. The term "nucleic acid" is synonymous with "polynucleotide" and is intended to include a gene, a cDNA molecule, an mRNA molecule, as well as a fragment of any of these such as an oligonucleotide, and further, equivalents thereof (explained more filly below). Sizes of nucleic acids are stated either as kilobases (kb) or base pairs (bp). These are estimates derived from agarose or polyacrylamide gel electrophoresis (PAGE), from nucleic acid sequences which are determined by the user or published. Protein size is stated as molecular mass in kilodaltons (kDa) or as length (number of amino acid residues). Protein size is estimated from PAGE, from sequencing, from presumptive amino acid sequences based on the coding nucleic acid sequence or from published amino acid sequences.

Specifically, cDNA molecules encoding the amino acid sequence corresponding to the HK-D3 polypeptide of the present invention, or active variants thereof, can be synthesized by the polymerase chain reaction (PCR) (see, for example, U.S. Pat. No. 4,683,202) using primers derived the sequence of the protein disclosed herein. These cDNA sequences can then be assembled into a eukaryotic or prokaryotic expression vector and the resulting vector can be used to direct the synthesis of the fusion polypeptide or its fragment or derivative by appropriate host cells, for example COS or CHO cells.

This invention includes isolated nucleic acids having a nucleotide sequence encoding the HK-D3 variant polypeptide used in transfecting cells in vitro or in vivo to express their polypeptide product. The term nucleic acid as used herein is intended to include such fragments or equivalents. The nucleic acid sequences of this invention can be DNA or RNA.

A cDNA nucleotide sequence encoding an HK-D3 polypeptide variant or derivative can be obtained by isolating total mRNA from an appropriate cell line. Double stranded cDNA is prepared from total mRNA. cDNA can be inserted into a suitable plasmid, bacteriophage or viral vector using any one of a number of known techniques.

In reference to a nucleotide sequence, the term "equivalent" is intended to include sequences encoding structurally homologous and/or a functionally equivalent proteins such as naturally occurring isoforms or related, immunologically cross-reactive family members of these proteins. Such isoforms or family members are defined as proteins that share function and amino acid sequence similarity to, for example, SEQ ID NO:1, 2 or 3.

The techniques for assembling and expressing DNA coding sequences include synthesis of oligonucleotides, PCR, transforming cells, constructing vectors, expression systems, and the like; these are well-established in the art such that those of ordinary skill are familiar with standard resource materials, specific conditions and procedures.

Expression Vectors and Host Cells

This invention includes an expression vector comprising a nucleic acid sequence encoding a HK-D3 polypeptide operably linked to at least one regulatory sequence.

The term "expression vector" or "expression cassette" as used herein refers to a nucleotide sequence which is capable of affecting expression of a protein coding sequence in a host compatible with such sequences. Expression cassettes include at least a promoter operably linked with the polypeptide coding sequence; and, optionally, with other sequences, e.g., transcription termination signals. Additional factors necessary or helpful in effecting expression may also be included, e.g., enhancers.

"Operably linked" means that the coding sequence is linked to a regulatory sequence in a manner that allows expression of the coding sequence. Known regulatory sequences are selected to direct expression of the desired protein in an appropriate host cell. Accordingly, the term "regulatory sequence" includes promoters, enhancers and other expression control elements. Such regulatory sequences are described in, for example, Goeddel, *Gene Expression Technology. Methods in Enzymology*, vol. 185, Academic Press, San Diego, Calif. (1990)).

Thus, expression cassettes include plasmids, recombinant viruses, any form of a recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g. a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA, e.g., plasmids, viruses, and the like (U.S. Pat. No. 5,217,879), and includes both the expression and nonexpression plasmids. Where a recombinant microorganism or cell culture is a host for an "expression vector," this includes both extrachromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

Those skilled in the art appreciate that the particular design of an expression vector of this invention depends on considerations such as the host cell to be transfected and the nature (e.g., size) of the polypeptide to be expressed.

The present expression vectors comprise the full range of nucleic acid molecules encoding the various embodiments of the HK-D3 polypeptide.

Such expression vectors are used to transfect host cells (in vitro, ex vivo or in vivo) for expression of the DNA and production of the encoded proteins which include fusion polypeptides. It will be understood that a genetically modified cell expressing the HK-D3 polypeptide may transiently express the exogenous DNA for a time sufficient for the cell to be useful for its stated purpose.

Host cells may also be transfected with one or more expression vectors that singly or in combination comprise DNA encoding the HK-D3 polypeptide and DNA encoding at least a portion of a second HK-D3-derived sequence (or variant), so that the host cells produce yet further HK-D3 polypeptides that include both the portions.

Methods for producing the HK-D3 polypeptide, are all conventional in the art. Cultures typically includes host cells, appropriate growth media and other byproducts. Suitable culture media are well known in the art. The HK-D3 polypeptide can be isolated from medium or cell lysates using conventional techniques for purifying proteins and peptides, including ammonium sulfate precipitation, fractionation column chromatography (e.g. ion exchange, gel filtration, affinity chromatography, etc.) and/or electrophoresis (see generally, *Meth Enzymol*, 22:233–577 (1971)). Once purified, partially or to homogeneity, the recombinant polypeptides of the invention can be utilized in pharmaceutical compositions as described in more detail herein.

The term "isolated" as used herein, when referring to a molecule or composition, means that the molecule or composition is separated from at least one other compound (protein, other nucleic acid, etc.) or from other contaminants with which it is natively associated or becomes associated during processing. An isolated composition can also be substantially pure. An isolated composition can be in a homogeneous state and can be dry or in aqueous solution. Purity and homogeneity can be determined, for example, using analytical chemical techniques such as polyacrylamide gel electrophoresis (PAGE) or high performance liquid chromatography (HPLC). It is understood that even where a protein has been isolated so as to appear as a homogenous or dominant band in a gel pattern, there are generally trace contaminants which co-purify with it.

Prokaryotic or eukaryotic host cells transformed or transfected to express the HK-D3 polypeptide are within the scope of the invention. For example, the HK-D3 polypeptide may be expressed in bacterial cells such as *E. coli*, insect cells (baculovirus), yeast, or mammalian cells such as Chinese hamster ovary cells (CHO) or human cells (which are preferred for human therapeutic use of the transfected cells). Other suitable host cells may be found in Goeddel, (1990) supra or are otherwise known to those skilled in the art.

Expression in eukaryotic cells leads to partial or complete glycosylation and/or formation of relevant inter- or intrachain disulfide bonds of the recombinant polypeptide.

Examples of vectors for expression in yeast *S. cerevsiae* include pYepSec1 (Baldari et al., (1987) *EMBO J.* 6:229–234), pMFa (Kujan et al. (1982) *Cell* 30:933–943), pJRY88 (Schultz et al., (1987) *Gene* 54:113–123), and pYES2 (Invitrogen Corporation, San Diego, Calif.). Baculovirus vectors available for expression of proteins in cultured insect cells (SF 9 cells) include the pAc series (Smith et al., (1983) *Mol. Cell Biol*, 3:2156–2165,) and the pVL series (Lucklow, V. A., and Summers, M. D., (1989) *Virology* 170:31–39). Generally, COS cells (Gluzman, Y., (1981) *Cell* 23:175–182) are used in conjunction with such vectors as pCDM 8 (Aruffo A. and Seed, B., supra, for transient amplification/expression in mammalian cells, while CHO (dhfr-negative CHO) cells are used with vectors such as pMT2PC (Kaufman et al. (1987), *EMBO J.* 6:187–195) for stable amplification/expression in mammalian cells. The NS0 myeloma cell line (a glutamine synthetase expression system.) is available from Celltech Ltd.

Often, in fusion expression vectors, a proteolytic cleavage site is introduced at the junction of the reporter group and the target protein to enable separation of the target protein from the reporter group subsequent to purification of the fusion protein. Proteolytic enzymes for such cleavage and their recognition sequences include Factor Xa, thrombin and enterokinase.

Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase, maltose E binding protein, or protein A, respectively, to the target recombinant polypeptide.

Inducible non-fusion expression vectors include pTrc (Amann et al., (1988) Gene 69:301–315) and pET 11d (Studier et al., Gene Expression Technology: Methods in Enzymology 185, Academic Press, San Diego, Calif (1990) 60–89). While target gene expression relies on host RNA polymerase transcription from the hybrid trp-lac fusion promoter in pTrc, expression of target genes inserted into pET 11d relies on transcription from the T7 gn10-lacO fusion promoter mediated by coexpressed viral RNA polymerase (T7gn1). Th is viral polymerase is supplied by host strains BL21(DE3) or HMS174(DE3) from a resident λ prophage harboring a T7gn1 under the transcriptional control of the lacUV 5 promoter.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and re-ligated in the form desired. The DNA sequences which form the vectors are available from a number of sources. Backbone vectors and control systems are generally found on available "host" vectors which are used for the bulk of the sequences in construction. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleotide derivatives. The entire gene sequence for genes of sizeable length, e.g., 500–1000 bp may be prepared by synthesizing individual overlapping complementary oligonucleotides and filling in single stranded non-overlapping portions using DNA polymerase in the presence of the deoxyribonucleotide triphosphates. This approach has been used successfully in the construction of several genes of known sequence. See, for example, Edge, M. D., Nature (1981) 292:756; Nambair, K. P., et al., Science (1984) 223:1299; and Jay, E., J Biol Chem (1984) 259:6311.

Synthetic oligonucleotides are prepared by either the phosphotriester method as described by references cited above or the phosphoramidite method as described by Beaucage, S L et al., Tetrahed Lett (1981) 22:1859; and Matteucci, M D et al., J Am Chem Soc (1981) 103:3185 and can be prepared using commercially available automated oligonucleotide synthesizers. Kinase treatment of single strands prior to annealing or for labeling is achieved using well-known methods.

Once the components of the desired vectors are thus available, they can be excised and ligated using standard restriction and ligation procedures. Site-specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. If desired, size separation of the cleaved fragments may be performed by polyacrylamide gel or agarose gel electrophoresis using standard techniques. A general description of size separations is found in Meth Enzymol (1980) 65:499–560.

Any of a number of methods are used to introduce mutations into the coding sequence to generate variants of the invention if these are to be produced recombinantly. These mutations include simple deletions or insertions, systematic deletions, insertions or substitutions of clusters of bases or substitutions of single bases. Modifications of the DNA sequence are created by site-directed mutagenesis, a well-known technique for which protocols and reagents are commercially available (Zoller, M J et al., Nuci Acids Res (1982) 10:6487–6500 and Adelman, J P et al., DNA (1983) 2:183–193)). The isolated DNA is analyzed by restriction and/or sequenced by the dideoxy nucleotide method of Sanger (Proc Natl Acad Sci USA (1977) 74:5463) as further described by Messing, et al., Nucleic Acids Res (1981) 9:309, or by the method of Maxam et al., Meth. Enzymol., supra.

Vector DNA can be introduced into mammalian cells via conventional techniques such as calcium phosphate or calcium chloride co-precipitation, DEAE-dextran-mediated transfection, lipofection, or electroporation. Suitable methods for transforming host cells can be found in Sambrook et al. supra and other standard texts. In fusion expression vectors, a proteolytic cleavage site is introduced at the junction of the reporter group and the target protein to enable separation of the target protein from the reporter group subsequent to purification of the fission protein. Proteolytic enzymes for such cleavage and their recognition sequences include Factor Xa, thrombin and enterokinase.

Promoters and Enhancers

A promoter region of a DNA or RNA molecule binds RNA polymerase and promotes the transcription of an "operably linked" nucleic acid sequence. As used herein, a "promoter sequence" is the nucleotide sequence of the promoter which is found on that strand of the DNA or RNA which is transcribed by the RNA polymerase. The preferred promoter sequences of the present invention must be operable in mammalian cells and may be either eukaryotic or viral promoters. Although preferred promoters are described in the Examples, other useful promoters and regulatory elements are discussed below. Suitable promoters may be inducible, repressible or constitutive. A "constitutive" promoter is one which is active under most conditions encountered in the cell's environmental and throughout development. An "inducible" promoter is one which is under environmental or developmental regulation. A "tissue specific" promoter is active in certain tissue types of an organism. An example of a constitutive promoter is the viral promoter MSV-LTR, which is efficient and active in a variety of cell types, and, in contrast to most other promoters, has the same enhancing activity in arrested and growing cells. Other preferred viral promoters include that present in the CMV-LTR (from cytomegalovirus) (Bashart, M. et al., Cell 41:521(1985)) or in the RSV-LTR (from Rous sarcoma virus) (Gorman, C M, Proc. Natl. Acad. Sci. USA 79:6777 (1982);. Also useful are the promoter of the mouse metallothionein I gene (Hamer, D., et al., J. Mol. Appl. Gen. 1:273–288 (1982)); the TK promoter of Herpes virus (McKnight, S., Cell 31:355–365 (1982)); the 5V40 early promoter (Benoist, C., et al., Nature 290:304–3 10 (1981)); and the yeast gal4 gene promoter (Johnston, S A, et al., Proc. Natl. Acad. Sci. (USA) 79:6971–6975 (1982); Silver, Pa., et al., Proc. Natl. Acad. Sci. (USA) 81:5951–5955 (1984)). Other illustrative descriptions of transcriptional factor association with promoter regions and the separate activation and DNA binding of transcription factors include: Keegan et al., Nature (1986) 231:699; Fields et al., Nature (1989) 340:245; Jones, Cell (1990) 61:9; Lewin, Cell (1990) 61:1161;

Ptashne et al., *Nature* (1990) 346:329; Adams et al., *Cell* (1993) 72:306. The relevant disclosure of all of these above-listed references is hereby incoroorated by reference.

The promoter region may further include an octamer region which may also function as a tissue specific enhancer, by interacting with certain proteins found in the specific tissue. The enhancer domain of the DNA construct of the present invention is one which is specific for the target cells to be transfected, or is highly activated by cellular factors of such target cells. Examples of vectors (plasmid or retrovirus) are disclosed in (Roy-Burman et al., U.S. Pat. No. 5,112,767). For a general discussion of enhancers and their actions in transcription, see, Lewin, B M, *Genes IV*, Oxford University Press, Oxford, (1990), pp. 552–576. Particularly useful are retroviral enhancers (e.g., viral LTR). The enhancer is preferably placed upstream from the promoter with which it interacts to stimulate gene expression. For use with retroviral vectors, the endogenous viral LTR may be rendered enhancer-less and substituted with other desired enhancer sequences which confer tissue specificity or other desirable properties such as transcriptional efficiency.

The nucleic acid sequences of the invention can also be chemically synthesized using standard techniques. Various methods of chemically synthesizing polydeoxynucleotides are known, including solid-phase synthesis which, like peptide synthesis, has been fully automated with commercially available DNA synthesizers (See, e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

Delivery of Nucleic Acid to Cells and Animals

DNA delivery involves introduction of a "foreign" DNA either (1) into a cell ex vivo and ultimately, into a live animal by administering the cells, or (2) directly into the animal. Several general strategies for "gene delivery" (i.e., delivery of any nucleic acid vector) for purposes that include "gene therapy" have been studied and reviewed extensively (Yang, N-S., *Crit. Rev. Biotechnol.* 12:335–356 (1992); Anderson, W F, *Science* 256:808–813 (1992); Miller, A S, *Nature* 357:455–460 (1992); Crystal, R G, *Amer. J. Med.* 92(suppl 6A):44S-52S (1992); Zwiebel, J A et al., *Ann. N.Y. Acad. Sci.* 618:394–404 (1991); McLachlin, J R et al., *Prog. Nucl. Acid Res. Molec. Biol.* 38:91–135 (1990); Kohn, D B et al., *Cancer Invest.* 7:179–192 (1989), which references are herein incorporated by reference in their entirety).

One approach comprises nucleic acid transfer into primary cells in culture followed by autologous transplantation of the ex vivo transformed cells into the host, either systemically or into a particular organ or tissue.

Preferred DNA molecules for delivery as described below encode HK-D3, e.g. SEQ ID NO:1, 2 or 3.

For accomplishing the objectives of the present invention, nucleic acid therapy would be accomplished by direct transfer of a the functionally active DNA into mammalian somatic tissue or organ in vivo. DNA transfer can be achieved using a number of approaches described below. These systems can be tested for successful expression in vitro by use of a selectable marker (e.g., G418 resistance) to select transfected clones expressing the DNA, followed by detection of the presence of the antigen-containing expression product (after treatment with the inducer in the case of an inducible system) using an antibody to the product in an appropriate immunoassay. Efficiency of the procedure, including DNA uptake, plasmid integration and stability of integrated plasmids, can be improved by linearizing the plasmid DNA using known methods, and co-transfection using high molecular weight mammalian DNA as a "carrier".

Examples of successful "gene transfer" reported in the art include: (a) direct injection of plasmid DNA into mouse muscle tissues, which led to expression of marker genes for an indefinite period of time (Wolff, J A et al., *Science* 247:1465 (1990); Acsadi, G. et al., *The New Biologist* 3:71 (1991)); (b) retroviral vectors are effective for in vivo and in situ infection of blood vessel tissues; (c) portal vein injection and direct injection of retrovirus preparations into liver effected gene transfer and expression in vivo (Horzaglou, M. et al., *J. Biol. Chem.* 265:17285 (1990); Koleko, M. et al., *Human Gene Therapy* 2:27 (1991); Ferry, N. et al., *Proc. Natl. Acad. Sci. USA* 88:8387 (1991)); (d) intrtracheal infusion of recombinant adenovirus into lung tissues was effective for in vivo transfer and prolonged expression of foreign genes in lung respiratory epithelium (Rosenfeld, M A et al., *Science* 252:431 (1991); (e) Herpes simplex virus vectors achieved in vivo gene transfer into brain tissue (Ahmad, F. et al., eds, *Miami Short Reports—Advances in Gene Technology: The Molecular Biology of Human Genetic Disease*, Vol 1, Boehringer Manneheim1 Biochemicals, USA, 1991). Gene therapy of cystic fibrosis using transfection by plasmids using any of a number of methods and by retroviral vectors has been described by Collins et al., U.S. Pat. No. 5,240,846.

Retroviral-mediated human therapy utilizes amphotrophic, replication-deficient retrovirus systems (Temin, H M, Human Gene Therapy 1:111(1990); Temin et al., U.S. Pat. No. 4,980,289; Temin et al., U.S. Pat. No. 4,650,764; Temin et al., U.S. Pat. No. 5,124,263; Wills, J W, U.S. Pat. No. 5,175,099; Miller, A D, U.S. Pat. No. 4,861,719). Such vectors have been used to introduce functional DNA into human cells or tissues, for example, the adenosine deaminase gene into lymphocytes, the NPT-II gene and the gene for tumor necrosis factor into tumor infiltrating lymphocytes. Retrovirus-mediated gene delivery generally requires target cell proliferation for gene transfer (Miller, D G et al., *Mol. Cell. Biol.* 10:4239 (1990)). This condition is met by certain of the preferred target cells into which the present DNA molecules are to be introduced, i.e., actively growing tumor cells. The DNA molecules encoding the HK-D3 polypeptide of the present invention may be packaged into retrovirus vectors using packaging cell lines that produce replication-defective retroviruses, as is well-known in the art (see, for example, Cone, R D et al., *Proc. Nati. Acad. Sci. USA* 81:6349–6353 (1984); Mann, R F et al., *Cell* 33:153–159 (1983); Miller, A D et al., *Molec. Cell. Biol.* 5:43 1–437 (1985); Sorge, J., et al., *Molec. Cell. Biol.* 4:1730–1737 (1984); Hock, R A et al., *Nature* 320:257 (1986); Miller, A D et al., *Molec. Cell. Biol.* 6:2895–2902 (1986)). Newer packaging cell lines which are efficient an safe for gene transfer have also been described (Bank et al., U.S. Pat. No. 5,278,056).

This approach can be utilized in a site specific manner to deliver the retroviral vector to the tissue or organ of choice. Thus, for example, a catheter delivery system can be used (Nabel, G. et al., *Science* 244:1342 (1989)). Such methods, using either a retroviral vector or a liposome vector, are particularly useful to deliver the nucleic acid to be expressed to a blood vessel wall, or into the blood circulation of a tumor.

Other virus vectors may also be used, including recombinant adenoviruses (Horowitz, M S, In: Virology, Fields, B N et al., eds, Raven Press, New York, 1990, p. 1679; Berkner, K L, Biotechniques 6:616–629, 1988), Strauss, S E, In: The Adenoviruses, Ginsberg, H S, ed., Plenum Press, New York, 1984, chapter 11), herpes simplex virus (HSV) for neuron-specific delivery and persistence. Advantages of adenovirus vectors for human gene delivery include the fact that recombination is rare, no human malignancies are known to be associated with such viruses, the adenovirus genome is double stranded DNA which can be manipulated to accept foreign genes of up to 7.5 kb in size, and live adenovirus is a safe human vaccine organisms. Adeno-associated virus is also useful for human therapy (Samulski, R J et al., EMBO J. 10:3941 (1991)) in the present invention.

Another useful vector, particularly in humans, is vaccinia virus, which can be rendered non-replicating (U.S. Pat. Nos. 5,225,336; 5,204,243; 5,155,020; 4,769,330; Sutter, G et al., *Proc. Nat. Acad. Sci. USA* (1992) 89:10847–10851; Fuerst, T R et al., *Proc. Natl. Acad. Sci. USA* (1989) 86:2549–2553; Falkner F G et al., *Nucl. Acids Res* (1987) 15:7192; Chakrabarti, S et al., *Molec. Cell. Biol.* (1985) 5:3403–3409). Descriptions of recombinant vaccinia viruses and other viruses containing heterologous DNA and their uses in immunization and DNA therapy are reviewed in: Moss, B., *Curr. Opin. Genet. Dev.* (1993) 3:8690; Moss, B. *Biotechnology* (1992) 20:345–362; Moss, B., *Curr Top Microbiol Immunol* (1992) 158:25–38; Moss, B., *Science* (1991) 252: 1662–1667; Piccini, A et al., *Adv. Virus Res.* (1988) 34:43–64; Moss, B. et al., *Gene Amplif Anal* (1983) 3:201–213.

In addition to naked DNA or RNA, or viral vectors, engineered bacteria may be used as vectors. A number of bacterial strains including *Salmonella*, BCG and *Listeria monocytogenes*(LM) (Hoiseth & Stocker, *Nature* 291, 238–239 (1981); Poirier, T P et al. *J. Exp. Med* 168, 25–32 (1988); (Sadoff, J C, et al., *Science* 240, 336–338 (1988); Stover, C K, et al., *Nature* 351, 456–460(1991); Aldovini, A. et al., *Nature* 351, 479–482 (1991); Schafer, R., et al., *J. Immunol.* 149, 53–59 (1992); Ikonomidis, G. et al., *J. Exp. Med.* 180, 2209–2218 (1994)). These organisms permit enteric routes of infection, providing the possibility of oral nucleic acid delivery.

In addition to virus-mediated gene transfer in vivo, physical means well-known in the art can be used for direct transfer of DNA, including administration of plasmid DNA (Wolff et al., 1990, supra) and particle-bombardment mediated gene transfer (Yang, N.-S., et al., *Proc. Natl. Acad. Sci. USA* 87:9568 (1990); Williams, R S et al., *Proc. Natl. Acad. Sci. USA* 88:2726 (1991); Zelenin, A V et al., *FEBS Lett.* 280:94 (1991); Zelenin, A V et al., FEBS Lett. 244:65 (1989); Johnston, S A et al., *In Vitro Cell. Dev. Biol.* 27:11 (1991)). Furthermore, electroporation, a well-known means to transfer genes into cell in vitro, can be used to transfer DNA molecules of the present invention to tissues in vivo (Titomirov, A V et al., *Biochim. Biophys. Acta* 1088:131 ((1991)).

"Carrier mediated gene transfer" has also been described (Wu, C H et al., *J. Biol. Chem.* 264:16985 (1989); Wu, G Y et al., *J. Biol. Chem.* 263:14621 (1988); Soriano, P. et al., *Proc. Natl. Acad. Sci. USA* 80:7128 (1983); Wang, C-Y. et al., *Proc. Natl. Acad. Sci. USA* 84:7851 (1982); Wilson, J M et al., *J. Biol. Chem.* 267:963 (1992)). Preferred carriers are targeted liposomes (Nicolau, C. et al., *Proc. Natl. Acad Sci. USA* 80:1068 (1983); Soriano et al., supra) such as immunoliposomes, which can incorporate acylated mAbs into the lipid bilayer (Wang et al., supra). Polycations such as asialoglycoprotein/polylysine (Wu et al., 1989, supra) may be used, where the conjugate includes a molecule which recognizes the target tissue (e.g., asialoorosomucoid for liver) and a DNA binding compound to bind to the DNA to be transfected. Polylysine is an example of a DNA binding molecule which binds DNA without damaging it. This conjugate is then complexed with plasmid DNA of the present invention for transfer.

Plasmid DNA used for transfection or microinjection may be prepared using methods well-known in the art, for example using the Quiagen procedure (Quiagen), followed by DNA purification using known methods, such as the methods exemplified herein.

Having now generally described the invention, the same will be more readily understood through reference to the following examples which are provided by way of illustration, and are not intended to be limiting of the present invention, unless specified.

EXAMPLE I

Figure 3:
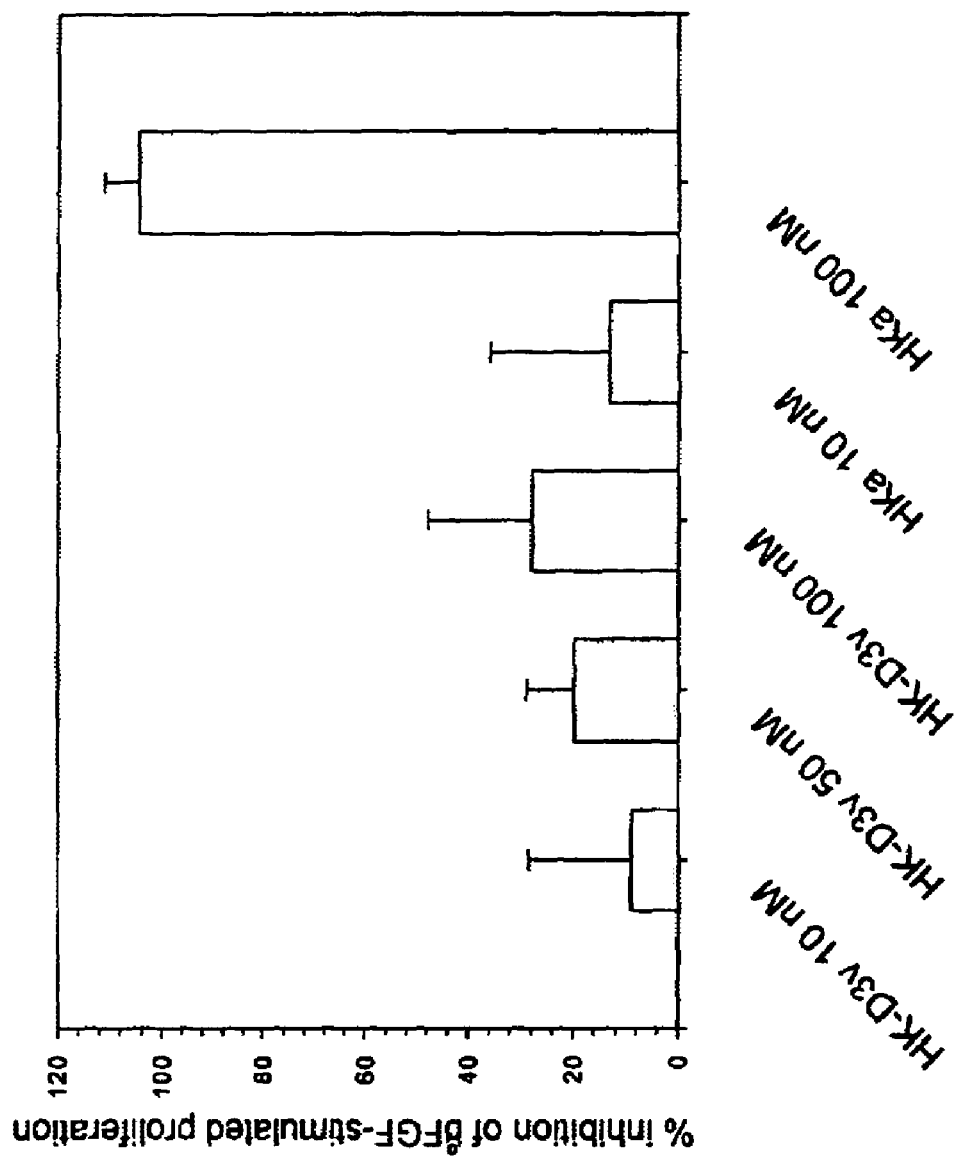
FIG. 3 shows the inhibition of EC proliferation by recombinant HK-D3v. HUVEC in EBM media (3,000 cells/well) were added to 96 well plates coated with gelatin. The cells were allowed to adhere for 4 hours at which time the EBM media was exchanged for EBM+bFGF (10 ng/mL) with or without the test inhibitor. The plates were allowed to incubate for 48 hours at which time the total cell number per each well was determined using the MTS assay (n=3 per each concentration of inhibitor).

Inhibition of Endothelial Cell Proliferation by HK-D3v bFGF was used to stimulate HUVEC proliferation. Cells were incubated in the presence of bFGF alone or with added inhibitors of proliferation for 48 hours in a 96 well plate. Proliferation is then measured using the chromogenic reagent, MTS. Results are shown in FIG. 3 as relative proliferation percent) compared to cells incubated with bFGF alone (set as 100% proliferation).

HK-D3v inhibited bFGF-stimulated proliferation of HUVEC in a dose dependent manner. Treatment of HUVEC treated with 0.1 μM HK-D3v did not affect cell viability, indicating that this polypeptide is not cytotoxic to these cells.

McCrae (WO 00/35407, Jun., 22, 2000)) described variants of the 8-mer peptide $X_1$ Asn-Asn-Ala-Thr-Phe-Tyr-Phe-Lys-$X_2$, (wherein $X_1$ and $X_2$ represented from zero to twelve additional amino acids of various sequence) that inhibit EC proliferation (and a cyclic Cys-Val-Gly-Cys peptide with a disulfide bond linking the two Cys residues, which does not inhibit EC proliferation). These peptides are all sequences derived from the sequence of native HK-D3. The 8-mer peptide was asserted to inhibit EC with an $IC_{50}<0.8$ μM. However, the present inventors discovered that this peptide precipitated serum proteins present in serum supplement used in the cell proliferation assay, which led to apoptosis. Thus, what was reported by McCrae to be inhibition of, proliferation was in fact an artifact of the precipitation phenomenon and subsequent induction of apoptosis. The actual $IC_{50}$ of the above 8-mer peptide for true inhibition of EC proliferation was >50 μM. This is in contrast to HK-D3 (and its HK-D3v variant) which were more than 200-fold more inhibitory ($IC_{50}$~0.25 μM see FIG. 3). Thus, it is concluded that the shorter peptides described by McCrae are not sufficient to recapitulate the anti-proliferative activity of full length HK-D3 indicating either that (a) the peptides need to be conformationally constrained within the larger HK-D3 structure or (b) additional, previously unidentified regions of HK-D3 are required for the full inhibitory activity against ECs observed by the present inventors.

EXAMPLE II

HK-D3v Inhibits Endothelial Cell Tube Formation of HUVECs on Matrigel®

HUVEC were seeded onto Matrigel®-coated 96 well plates for testing of the inhibition of tube formation by the compounds of this invention. FIGS. 4 and 5 are photomicrographs showing the results.

Endothelial cell tube formation on Matrigel® was stimulated by incubation for 24 hr with either FGF-2 (10 ng/ml ) (FIG. 4A) or FGF-2 (20 ng/ml), or a mixture of VEGF (20 ng/ml) and PMA (40 ng/ml) (FIG. 5A). Addition of 250 nM HK-D3 caused disruption of tube formation under these conditions (FIGS. 4B and 5B).

EXAMPLE III

Figure 6:
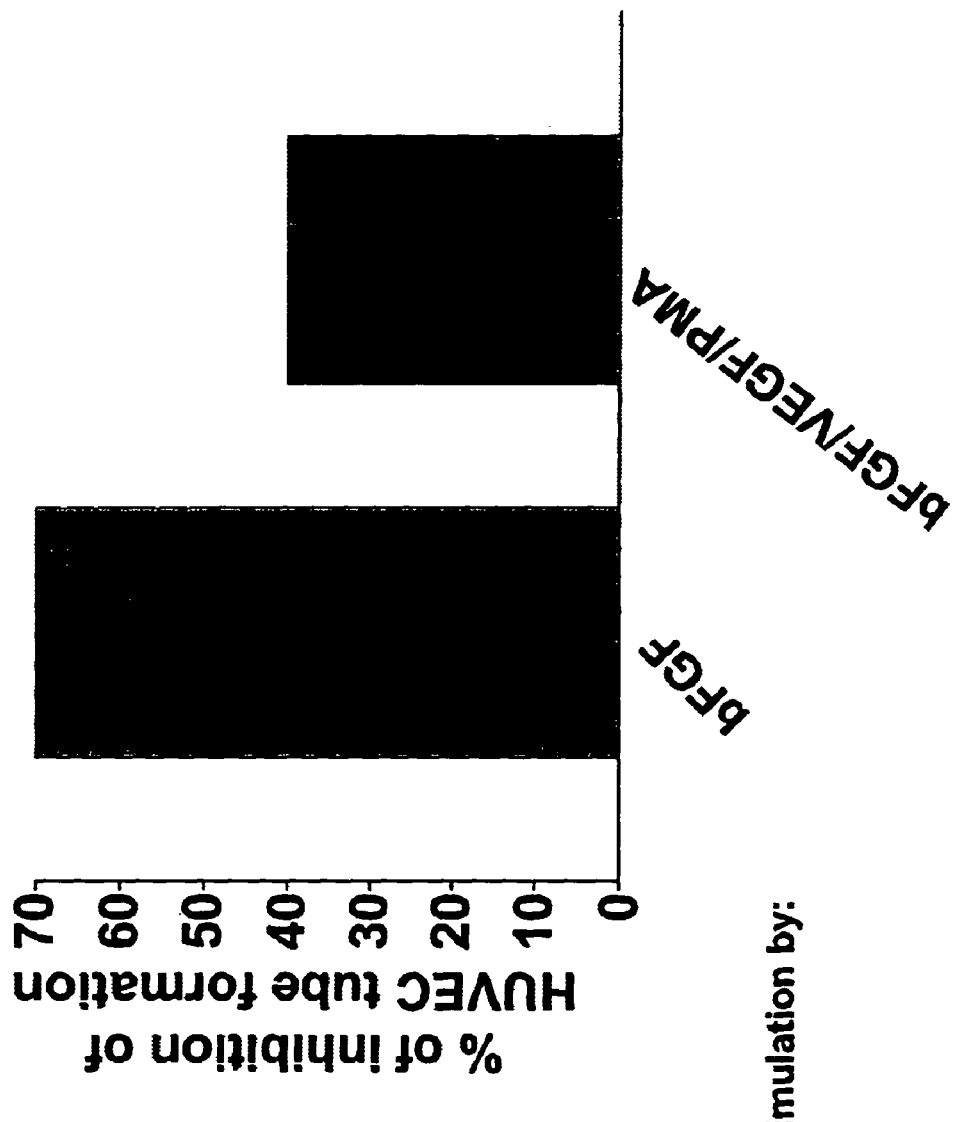
FIG. 6 is a graphic representation that quantitates the inhibition of tube formation shown in FIGS. 4A/4B and 5A/5B.
Figure 7:
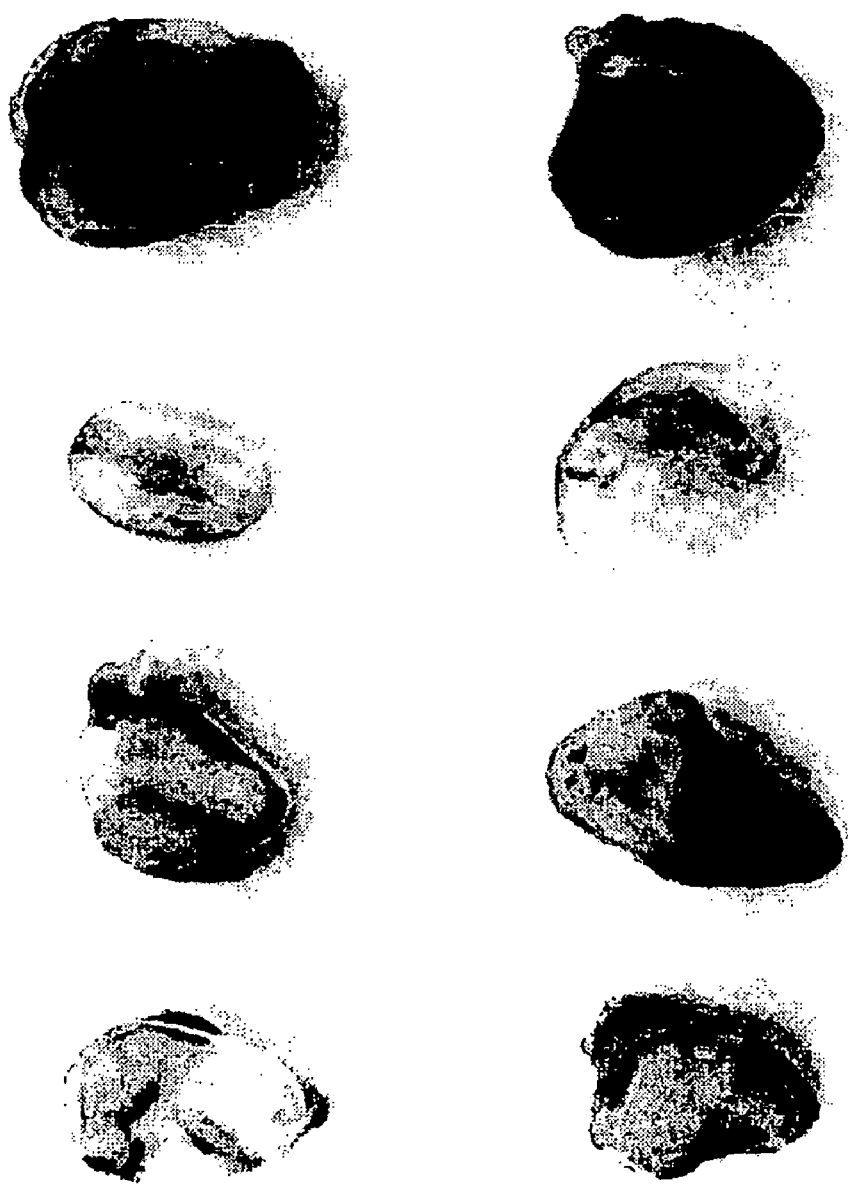
FIG. 7 shows that HK-D3v (10 and 30 μg per 0.5 ml plug) inhibited the growth of the rat prostate carcinoma MatLyLu ("MLL") tumor in vivo in the Matrigel® plug model. n=3.

HK-D3v Inhibits Tumor Cell-Mediated Tumor Growth and Angiogenesis In Vivo in a Matrigel® Plug Model The rat prostate tumor cell line (MatLyLu abbreviated MLL) was used to stimulate angiogenesis in the Matrigel® plug model described above. In this study, tumor growth and angiogenesis were evaluated Results are shown in FIGS. 6, 7 and 8.

Control plugs were inoculated with MLL tumor cells alone. Introduction of HK-D3v (at 1.8 or 4.3 μM) together with the tumor cells caused significant diminution of tumor weight (FIG. 7A) and angiogenesis (FIG. 7B).

The references cited above are all incorporated by reference herein, whether specifically incorporated or not.

Having now fully described this invention, it will be appreciated by those skilled in the art that the same can be performed within a wide-range of equivalent parameters, concentrations, and conditions without departing from the spirit and scope of the invention and without undue experimentation.

What is claimed is:

1. An isolated anti-angiogenic polypeptide that is:
   (a) a variant of native HK-D3 (SEQ ID NO: 1) designated HK-D3v, which has the amino acid sequence SEQ ID NO: 3, or
   (b) a variant of native HK-D3 (SEQ ID NO: 1) that has an N-terminal addition and has the sequence SEQ ID NO: 2, which polypeptide has at least 20% of the activity of native HK-D3 (SEQ ID NO: 1) in inhibiting angiogenesis, endothelial cell proliferation or endothelial tube formation in an in vitro or in vivo bioassay.

2. The isolated polypeptide of claim 1, which has the sequence SEQ ID NO: 3.

3. A diagnostically labeled anti-angiogenic polypeptide comprising the polypeptide according to claim 1 to which is conjugated a detectable diagnostic label.

4. A diagnostic HK-D3-related composition comprising:
   (a) the detectably labeled polypeptide of claim 3; and
   (b) a diagnostically acceptable carrier.

5. The composition of claim 4 wherein the detectable label is selected from the group consisting of a radionuclide, a PET-imageable agent, an MRI-imageable agent, a fluorescer, a fluorogen, a chromophore, a chromogen, a phosphorescer, a chemiluminescer and a bioluminescer.

6. The composition of claim 5, wherein the detectable label is a radionuclide selected from the group consisting of $^3$H, $^{14}$C, $^{35}$S, $^{67}$Ga, $^{68}$Ga, $^{72}$As, $^{89}$Zr, $^{97}$Ru, $^{99}$Tc, $^{111}$In, $^{123}$I, $^{125}$I, $^{131}$I, $^{169}$Yb and $^{201}$Tl.

7. The composition of claims 5 wherein the detectable label is a fluorescer or fluorogen selected from the group consisting of fluorescein, rhodamine, dansyl, phycoerythrin, phycocyanin, allophycocyanin, o-phthaldehyde, fluorescamine, a fluorescein derivative, Oregon Green, Rhodamine Green, Rhodol Green and Texas Red.

8. An anti-angiogenic pharmaceutical composition comprising:

(a) an anti-angiogenic effective amount of the polypeptide of claim 1, and
   (b) a pharmaceutically acceptable carrier.

9. The pharmaceutical composition of claim 8 in a form suitable for injection.

10. A therapeutically labeled anti-angiogenic polypeptide comprising a polypeptide according to claim 1 to which is bound a therapeutically active moiety.

11. A therapeutic anti-angiogenic pharmaceutical composition comprising:
    (a) an effective amount of the polypeptide of claim 10 to which the therapeutically active moiety is bound directly or indirectly; and
    (b) a therapeutically acceptable carrier.

12. The therapeutic composition of claim 11 wherein the therapeutically active moiety is a radionuclide.

13. The therapeutic composition of claim 12, wherein the radionuclide is selected from the group consisting of $^{47}$Sc, $^{67}$Cu, $^{90}$Y, $^{109}$Pd, $^{125}$I, $^{131}$I, $^{186}$Re, $^{188}$Re, $^{199}$Au, $^{211}$At, $^{212}$Pb and $^{217}$Bi.

14. The therapeutic composition of claim 11 in a form suitable for injection.

15. An affinity matrix for binding to or isolating an HK-D3-binding molecule or cells expressing the binding molecule, comprising the polypeptide of claim 1 immobilized to a solid support or carrier.

16. A method for isolating a HK-D3-binding molecule from a complex mixture comprising:
    (a) contacting the mixture with an affinity matrix of claim 15;
    (b) allowing material in the mixture to bind to the matrix;
    (c) removing unbound material from the matrix; and
    (d) eluting the bound HK-D3-binding molecule, thereby isolating said HK-D3-binding molecule.

17. A method for isolating or enriching cells expressing a HK-D3-binding site or receptor from a cell mixture, comprising (a) contacting the cell mixture with the affinity matrix of claim 15;
(b) allowing any cells expressing the binding site or receptor to bind to the affinity matrix;
(c) separating cells bound to the affinity matrix from unbound cells; and
(d) removing the bound cells from the affinity matrix, thereby isolating or enriching the HK-D3 binding site-expressing cells.

\* \* \* \* \*